US011993768B2

United States Patent
Leuthold et al.

(10) Patent No.: US 11,993,768 B2
(45) Date of Patent: May 28, 2024

(54) MODULAR PROCESSING SYSTEM AND METHOD FOR THE MODULAR CONSTRUCTION OF A PROCESSING SYSTEM

(71) Applicant: Sartorius Stedim Biotech GmbH, Goettingen (DE)

(72) Inventors: Martin Leuthold, Goettingen (DE); Stefan Weisshaar, Adelebsen (DE)

(73) Assignee: SARTORIUS STEDIM BIOTECH GMBH, Goettingen (DE)

(*) Notice: Subject to any disclaimer, the term of this patent is extended or adjusted under 35 U.S.C. 154(b) by 777 days.

(21) Appl. No.: 17/126,591

(22) Filed: Dec. 18, 2020

(65) Prior Publication Data
US 2021/0102155 A1 Apr. 8, 2021

Related U.S. Application Data

(63) Continuation of application No. PCT/EP2019/064747, filed on Jun. 6, 2019.

(30) Foreign Application Priority Data

Jun. 19, 2018 (DE) ..................... 10 2018 004 909.5

(51) Int. Cl.
*B01D 65/02* (2006.01)
*C07K 1/36* (2006.01)
(Continued)

(52) U.S. Cl.
CPC ............. *C12M 29/04* (2013.01); *B01D 65/02* (2013.01); *C07K 1/36* (2013.01); *C12M 23/44* (2013.01); *C12M 41/40* (2013.01)

(58) Field of Classification Search
CPC ...... C12M 29/04; C12M 23/44; C12M 41/40; C12M 29/00; C12M 23/58; C12M 29/14; B01D 65/02; C07K 1/36
See application file for complete search history.

(56) References Cited

U.S. PATENT DOCUMENTS 4,678,578 A * 7/1987 Nodes ..................... B01D 36/02
55/497
5,593,580 A 1/1997 Kopf
(Continued)

FOREIGN PATENT DOCUMENTS

DE 3441249 A1 5/1985
DE 102005008924 A1 * 8/2006 ........... B01D 25/001
(Continued)

OTHER PUBLICATIONS

International Search Report, PCT/EP2019/064747, dated Sep. 19, 2019, 3 pages.

*Primary Examiner* — Waqaas Ali
(74) *Attorney, Agent, or Firm* — Edell, Shapiro & Finnan, LLC

(57) ABSTRACT

A modular processing system (100) for biopharmaceutical processes includes (i) at least one first and at least one second processing unit (30, 32), which can be fluidically connected to each other; and (ii) at least one adapter plate (200), through which at least one fluid flow (14), flowing from the first processing unit (30) to the second processing unit (32), can flow. The adapter plate deflects the fluid flow between the first processing unit and the second processing unit at least partially; and/or controls the fluid flow, preferably, the pressure thereof, in an open loop or closed loop manner. A method for the modular construction of a processing system (100) for biopharmaceutical processes is also disclosed.

13 Claims, 14 Drawing Sheets

(51) Int. Cl.
  *C12M 1/00*    (2006.01)
  *C12M 1/34*    (2006.01)
  *C12M 3/00*    (2006.01)

(56) References Cited

U.S. PATENT DOCUMENTS

| | | |
|---|---|---|
| 2008/0041795 A1 | 2/2008 | Thalmann et al. |
| 2014/0291242 A1 | 10/2014 | Notzke et al. |
| 2017/0056825 A1 | 3/2017 | Schwan et al. |
| 2019/0030486 A1 | 1/2019 | Leuthold et al. |

FOREIGN PATENT DOCUMENTS

| | | |
|---|---|---|
| DE | 102005008924 A1 | 8/2006 |
| DE | 102011079647 A1 | 1/2013 |
| DE | 102012022540 A1 | 5/2014 |
| DE | 102016004115 A1 | 10/2017 |
| EP | 0111620 A2 | 6/1984 |
| EP | 0154845 A2 | 9/1985 |
| EP | 2907565 A1 | 8/2015 |

* cited by examiner

MODULAR PROCESSING SYSTEM AND METHOD FOR THE MODULAR CONSTRUCTION OF A PROCESSING SYSTEM

CROSS REFERENCE TO RELATED APPLICATIONS

This is a Continuation of International Application PCT/EP2019/064747 which has an international filing date of Jun. 6, 2019, and the disclosure of which is incorporated in its entirety into the present Continuation by reference. This Continuation also claims foreign priority under 35 U.S.C. § 119(a)-(d) to and also incorporates by reference, in its entirety, German Patent Application DE 10 2018 004 909.5 filed on Jun. 19, 2018.

FIELD OF THE INVENTION

The present invention relates to a modular processing system for biopharmaceutical processes and to a method for the modular construction of a processing system for biopharmaceutical processes.

BACKGROUND

Processes, such as, for example, cell separation (for example, by depth filtration), sterile filtration, chromatography steps, viral inactivation, virus filtration and/or crossflow filtration, are known from the biopharmaceutical industry. All of these processes constitute basic operations that are routinely combined to form various complete processes. In the prior art different filter systems or, more specifically, filter equipment are used, for example, for this purpose with regard to filtration processes. These filter systems, which are respectively responsible for working up the various process steps, are linked to one another. In this respect communication between the various filter systems is necessary, in order to match product flows and manipulated variables in the process accordingly. Furthermore, only standard filter units are used in the prior art (see, for example, DE 34 41 249 C2).

SUMMARY

Therefore, one object of the present invention is to provide a processing system for biopharmaceutical processes that enables a simplified and more compact combination of process steps.

In accordance with a first aspect of the invention, this object is achieved with a modular processing system for biopharmaceutical processes, said modular processing system comprising:
at least one first and second processing unit, which can be fluidically connected to each other;
at least one adapter plate, through which at least one fluid flow, flowing from the first processing unit to the second processing unit, can flow; wherein the adapter plate is configured such that the fluid flow between the first processing unit and the second processing unit can be deflected at least partially with the aid of the adapter plate; and/or the fluid flow, preferably, the pressure thereof, can be controlled in an open loop or closed loop manner with the aid of the adapter plate.

The term "processing unit" is to be understood, in particular, as meaning a unit, within which a specific process step for the desired process is carried out. In particular, a separation of components of a fluid flow takes place within a processing unit. For example, a processing unit may be a unit for cell separation (for example, by depth filtration), for sterile filtration, for a chromatography step, for viral inactivation or for crossflow filtration. As in the prior art, the processing unit can be selected as a standard processing unit with the desired specifications. The first and second processing unit may be identical or have at least partially different properties. For example, the size of the first and second processing unit may vary, but the first and second processing unit can still be easily connected to one another or, more specifically, combined, nevertheless, with the aid of the adapter plate. Preferably different processing units are connected to one another in one processing system, where in this case, for example, said processing units use different separating media or are responsible for different processing steps of a method. Identical processing units can then be used, if a capacity expansion is desired.

The adapter plate is connected between the first processing unit and the second processing unit in relation to the fluid flow and, as a result, fluidically connects the first processing unit and the second processing unit.

The adapter plate, which can be switched (at least partially) between two processing units in a modular processing system, can be used to carry out the necessary adaptations with respect to the fluid flow. Such adaptations allow the processing units (in particular, standard processing units) to be fluidically connected to one another. In this case the fluid flow can be redirected or, more specifically, deflected or rather changed correspondingly at least partially in the direction of flow; and/or the fluid flow can be controlled in an open loop or closed loop manner with the aid of the adapter plate, preferably or rather, in particular, the pressure thereof, with which the fluid impinges on the second processing unit. However, both adaptations can also be carried out simultaneously within one adapter plate.

Hence, at least one adapter plate can be arranged between two successive processing units in a processing system, in order to be able to make the necessary adaptations with respect to the fluid flow.

A combination of process steps on the basis of a modularly constructed processing system with at least one adapter plate between two processing units makes it possible to combine any and all process steps in one processing system, so that the need for setup space and system components can be reduced. The necessary investments are correspondingly reduced. Furthermore, such an arrangement enables, in particular, a compact and/or flexible combination for the continuous operating mode in a processing system, including the monitoring of a plurality of basic operations.

The processing system comprises preferably a plurality of first processing units connected in parallel and/or a plurality of second processing units connected in parallel, wherein the first processing units and the second processing units each form a processing unit group.

In other words, a plurality of successively connected processing units, which are connected without an adapter plate, are referred to as a processing unit group. Within a processing unit group the processing units are preferably connected in parallel. Therefore, an adapter plate of the present invention can be used to connect a processing unit group with a processing unit or two processing unit groups to one another.

The adapter plate has preferably an adapter channel, through which the fluid flow can flow, wherein the fluid flow can flow into the adapter channel through at least one inlet opening and can flow out through at least one outlet opening.

The "adapter channel" is to be understood, in particular, as meaning a channel through or, more specifically, in the adapter plate. The fluid flow, flowing from the first processing unit to the second processing unit, can flow through said adapter channel. The adapter channel is preferably a deflection channel.

The adapter channel has preferably an apparatus for venting and/or does not need any seals, which are usually needed in processing units.

Furthermore, it is preferred that the at least one inlet opening be arranged in such a way that it can be connected to an outflow channel of the first processing unit and/or wherein the at least one outlet opening is arranged in such a way that the said at least one outlet opening can be connected to an inflow channel of the second processing unit.

In particular, the "outflow channel" of the first processing unit is to be understood as meaning the channel, through which a fluid flow can emerge from the first processing unit. If the processing system has a plurality of first processing units, then the outflow channel, which is coupled to the adapter channel, is the outflow channel of the first processing unit, which is arranged directly upstream of the adapter plate. If the first processing unit is, for example, a filter unit, then the fluid, which emerges from the first processing unit through the outflow channel may be a filtrate, i.e., the fluid that is filtered by the first processing unit. If the first processing unit is a crossflow filtration unit, then the fluid, which emerges from the first processing unit through the outflow channel may also be a retentate (i.e., an unfiltered portion of the fluid flow). Thus, in the context of the crossflow filtration, either the filtrate or the retentate flows from the first processing unit through the adapter plate to the second processing unit, in order to be further processed there.

The "inflow channel" of the second processing unit is understood, in particular, as meaning the channel, through which the fluid flow flows out of the adapter plate into the second processing unit. If the processing system has a plurality of second processing units, then the inflow channel, which is coupled to the adapter channel, is the inflow channel of the second processing unit, which is connected directly downstream of the adapter plate. If the second processing unit is a filter unit, then this fluid flow corresponds to the feed liquid that is to be filtered by the second processing unit.

As a result of such a combination of the first processing unit with the second processing unit, two processing units can be connected in series to one another in a compact manner.

The adapter plate has preferably at least two inlet openings and at least two outlet openings, wherein at least one first inlet opening is arranged in such a way that the fluid flow can flow out of an outflow channel of the first processing unit into the adapter channel, wherein at least one second inlet opening is arranged in such a way that the fluid flow can flow out of an inflow channel of the first processing unit into the adapter channel, wherein at least one first outlet opening is arranged in such a way that the fluid flow can flow out of the first outlet opening into an outflow channel of the second processing unit, and wherein at least one second outlet opening is arranged in such a way that the fluid flow can flow out of the second outlet opening into an inflow channel of the second processing unit.

Furthermore, it is preferred that the adapter channel comprise:
a first channel region, which is arranged between the first inlet opening and the first outlet opening;
a second channel region, which is arranged between the second inlet opening and the second outlet opening; and
a connecting channel region, which fluidically connects the first and second channel region.

Preferably at least one deflection element is arranged displaceably in the adapter channel in such a way that a fluid flow can be deflected by the adapter plate in such a way that either:
a first fluid flow can flow into the adapter channel through the first inlet opening and can flow out through the first outlet opening; and a second fluid flow can flow into the adapter channel through the second inlet opening and can flow out of the adapter channel through the second outlet opening;
or:
a fluid flow can flow into the adapter channel through the first inlet opening and can flow out of the adapter channel through the second outlet opening.

The deflection element is arranged preferably in such a way that the deflection element can be pushed into the connecting channel region, in order to block a fluid flow through the connecting channel region. If the objective is to allow a fluid flow through the connecting channel region, then the deflection element can be pushed at least partially out of the connecting channel region. The deflection element closes preferably the connecting channel region in a fluid-tight manner. One possible embodiment of the deflection element is a displaceable closure plate. Preferably the deflection element can be displaced manually and/or automatically with an external controller. When the deflection element closes the connecting channel region, both processing units are connected in parallel.

Furthermore, in each case one deflection element can be arranged in the first channel region and/or the second channel region. Said deflection element is pushed into the corresponding channel region in such a way that the first outlet opening and/or the second inlet opening can be blocked by the respective deflection element. If said openings are blocked by the deflection elements, then the first and second filter unit are connected in series. Here, however, the deflection element in the connecting region is in a retracted position, so that a fluid flow through the connecting channel region is possible.

The displacement of the deflection elements is preferably coupled to one another. If, for example, the deflection element is opened in the connecting channel region, then the deflection elements close in the first and second channel region and vice versa.

The modular processing system comprises preferably two deflection elements that are configured as a multiway valve, wherein a first valve is arranged in the first channel region and a second valve is arranged in the second channel region, wherein the valves are configured such that either:
a first fluid flow can flow into the adapter channel through the first inlet opening and can flow out through the first outlet opening; and a second fluid flow can flow into the adapter channel through the second inlet opening and can flow out of the adapter channel through the second outlet opening;
or:
a fluid flow can flow into the adapter channel through the first inlet opening and can flow out of the adapter channel through the second outlet opening.

An alternative variant to the displaceable deflection element is provided with the aid of the valves in such a way that said alternative variant also makes it possible in a simple and compact manner to connect the first and second processing unit in series or in parallel. The valves are controlled preferably by an external control unit. The two valves can be controlled separately or together.

In a preferred embodiment the multiway valve comprises a valve tube, which in each case is arranged displaceably (in particular, rotatably) in the first and second channel region and through which the first and second fluid flow can flow in a corresponding manner, wherein at least two valve openings are arranged in a lateral surface of the valve tube, said valve openings being arranged so as to be offset from one another in the direction of displacement (in particular, direction of rotation), so that a fluid flow through the adapter channel can be deflected as a function of the displacement position (in particular, the rotational position) of the valve tube in the respective channel region.

The valve tube extends in each case at least partially in the first and second channel region and can be displaced, in particular, so as to be turnable or, more specifically, rotatable, there. A displacement (in particular, rotation) can be carried out manually and/or by an external control device. At least two valve openings are formed in the lateral surface of the valve tube. Said two valve openings are arranged so as to be offset from one another in relation to the direction of displacement (in particular, the direction of rotation) in such a way that a first fluid flow and/or a second fluid flow is made possible in a first position of the valve tube. That means, for example, that the first fluid flow enters the valve tube through the first inlet opening of the adapter plate through a first valve opening, which overlaps at least partially the first inlet opening. The second valve opening overlaps at least partially the first outlet opening so that the first fluid flow can flow out of the adapter plate through the first outlet opening. This applies correspondingly to the second fluid flow. A fluid flow through the connecting channel region is blocked based on the position of the valve openings in the respective channel regions, since no valve opening overlaps the connecting channel region. Since, however, the first and second fluid flow is permitted by the multiway valves, the first and second filter unit are connected in parallel.

However, the valve tubes have preferably at least three valve openings. Said three valve openings are arranged in such a way that in a first displacement position (in particular, position of rotation) of the valve tube, at least two valve openings are aligned in such a way that the first and second fluid flows, described above, are permitted; and, as a result, the first and second processing unit are connected in parallel. However, a fluid flow through the connecting channel region is blocked here, since no valve opening overlaps the connecting channel region.

However, as a result of the arrangement of the at least three valve openings, in a second displacement position (in particular, the position of rotation) of the respective valve tube, either the passage to an inlet opening or to an outlet opening is blocked, while access to the connecting channel region is permitted. This arrangement makes it possible, in particular, to connect the first and second processing unit in series.

In other words, in a serial connection the multiway valves are to be oriented in such a way that a fluid flow can enter the first valve tube through the first inlet opening of the adapter plate and through a valve opening, which overlaps at least partially the first inlet opening. The fluid flow can flow into the connecting channel region through a valve opening, which overlaps at least partially the connecting channel region. The passage to the first outlet opening is blocked by the valve tube, since no valve opening overlaps the first outlet opening. Then the fluid flow can flow into the second valve tube through a valve opening of the second valve tube, where said valve opening overlaps at least partially the connecting channel region. The fluid flow can flow out of the adapter plate through a valve opening in the second valve tube, where said valve opening overlaps at least partially the second outlet opening of the adapter plate. The passage to the second inlet opening is blocked by the valve tube, since no valve opening overlaps the second inlet opening.

In other words, the valve tube acts as a shut-off cock, which blocks or releases, as required, certain passage paths through the adapter plate.

At least one sensor is arranged preferably in or, alternatively, on the adapter channel. The sensor can be used to measure the pressure, the volume flow, the UV value, the pH value, the turbidity and/or the viscosity of the fluid, flowing through the adapter plate. In particular, inexpensive disposable sensors can be used for this purpose. The measured values can be used in turn to control in an open loop and/or closed loop manner the process, for example, the filtration process. For this purpose the measured values can be transmitted to an external control device, in order to be processed there and subsequently to be able to carry out corresponding measures.

Furthermore, it is preferred that the adapter channel be formed with at least one auxiliary input and/or auxiliary output.

With the aid of the at least one auxiliary input and/or auxiliary output, the fluid flow, which can flow through the adapter plate, can be at least partially discharged out of the adapter plate and/or fed back again. This branched fluid flow can be used, for example, for external processing of the fluid flow from at least one upstream processing step or filtration step during (continuous) viral inactivation (for example, viral inactivation after the protein A chromatography step). Furthermore, an external pump can be connected with an auxiliary input; and/or an integrity test can be carried out on different processing units within the processing system. In addition, the fluid flow can be discharged out of the first processing unit through an auxiliary output, in order to be able to be buffered and/or regenerated externally in the interim. Furthermore, a first processing unit can be cleaned separately through an auxiliary input. This means that, for example, the washing solution can flow out of the first processing unit through the auxiliary output in the adapter plate without contaminating the following processing step or, more specifically, the following processing unit. The washing solution may be, for example, a lye or a washing buffer. Furthermore, a diafiltration medium for solvent exchange can be fed through an auxiliary input. In principle, any other form of a media addition through an auxiliary input is possible. In particular, an elution/washing/cleaning of an upstream or downstream chromatography filter apparatus can be carried out through an auxiliary output. Furthermore, the processing system can be vented though the auxiliary output; and/or samples can be taken.

A plurality of auxiliary inputs and/or auxiliary outputs, which fulfill different or the same functions, can be provided in an adapter plate.

At least one pump is arranged preferably in or, alternatively, on the adapter channel.

A pump, which is integrated in the adapter plate, can facilitate, for example, sufficient processing performance, in particular, the filtration performance in the second or rather next processing unit. This feature is necessary, in particular, in a series circuit, in order to overcome the flow resistance of the next processing unit/filter unit.

In this case pumps that are also suitable include disposable designs that are cost effective to produce and do not incur any cleaning costs or, more specifically, maintenance costs.

In preferred embodiments the pump is a peristaltic pump or piston pump.

A peristaltic pump, also called a hose pump, is a positive displacement pump, in which the external mechanical deformation of a hose causes the fluid to be conveyed to be forced through said hose. The hose is supported on the outside of a housing of a pump head and can be clamped from the inside by rollers and/or sliding blocks, which rotate on a rotor (radial active system) or, alternatively, through a camshaft (linear or even horizontal active system). In both types of construction the motion results in a pinch point moving along the hose and, in this way, propels the fluid to be conveyed forward.

The peristaltic pump is arranged preferably in the connecting channel region.

Similarly a piston pump is a positive displacement pump, in which a displacer (piston) executes a stroke motion, i.e., a rectilinear (translatory) motion. The piston pump has a piston, which runs in a cylinder, combined with an inlet and an outlet, each of which can be closed by a valve.

The piston pump is arranged preferably in or, alternatively, on the connecting channel region of the adapter plate. A section in the connecting channel region is separated in the direction of flow by an intake valve and by an exhaust valve. The fluid can flow into this section through the intake valve and escape through the exhaust valve. The cylinder, in which the piston is mounted and can perform a translatory motion therein, is arranged in such a way that the cylinder is arranged on the connecting channel region and is fluidically connected thereto. In particular, the cylinder is arranged between the intake valve and the exhaust valve on the connecting channel region.

In a first cycle during suction, the piston executes a rearward motion, i.e., a motion away from the connecting channel region. The intake valve opens; and the fluid to be conveyed can flow into the connecting channel region or, more specially, the cylinder. In a second cycle during the conveying motion, the intake valve closes; and the piston moves in the direction of the connecting channel region. The exhaust valve opens; and the medium to be conveyed is pushed out.

At least one flow limiter is arranged preferably in the adapter channel.

In some filtration processes, regulation of the flow and/or pressure is advantageous. For example, it may be necessary to block or reduce the throughflow to the second processing unit/filter unit, in order to prevent an excessively high input pressure. Furthermore, the required transmembrane pressure in an upstream single-pass tangential flow filtration unit can be set by the flow limiter. In this case "single pass" describes the mode of operation in cross flow filtration, in which a fluid flow is processed without recirculation, in contrast to a standard mode of operation.

The at least one flow limiter is arranged in the adapter channel, preferably in the connecting channel region. This flow limiter can be fashioned as a valve.

In accordance with another aspect of the invention, the problem, on which the invention is based, is addressed with a method for the modular construction of a processing system, said method comprising the following steps of:
  providing at least one first and second processing unit;
  providing at least one adapter plate that is configured to fluidically connect the first and second processing unit, so that at least one fluid flow can flow from the first processing unit to the second processing unit through the adapter plate; and
  connecting the first and second processing unit to the adapter plate,
  wherein the adapter plate is selected and/or adjusted in such a way that the fluid flow between the first processing unit and the second processing unit can be at least partially deflected in a predefined manner with the aid of the adapter plate; and/or the fluid flow, preferably the pressure thereof, can be controlled in an open loop or closed loop manner in a predefined manner with the aid of the adapter plate.

These and other goals, features and advantages of the present invention will become more apparent from a study of the following detailed description of preferred embodiments and the accompanying drawings. Furthermore, it should also be noted that although embodiments are described separately, individual features of these embodiments can be combined to form additional embodiments.

DETAILED DESCRIPTION

Various processing units, which can be used within the scope of the present invention, exist for biopharmaceutical processes. FIGS. 1A through 1E show a basic construction of various processing units, which can be used within the scope of the present invention. In this context said processing units constitute a selection, but not an exhaustive list.

Figure 1A:
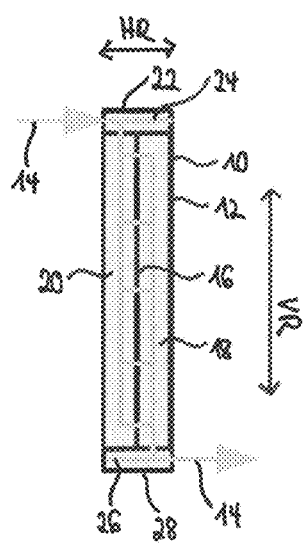
FIGS. 1A-1E show basic constructions of various processing units for biopharmaceutical processes, namely of a first type of filtration unit (FIG. 1A), a multilayer filtration unit (FIG. 1B), a precoat filtration unit (FIG. 1C), a filtration unit for chromatography (FIG. 1D), and a unit suitable e.g., for crossflow filtration (FIG. 1E)

FIG. 1A shows a processing unit 10 that can be used to take over a certain filtration step in a biopharmaceutical process. For this purpose the processing unit 10 has a processing housing 12, through which a fluid flow 14 can flow. The fluid flow 14 comprises the medium to be filtered. At least one filter medium 16 is arranged in the processing housing 12. Said filter medium comprises a porous material that is then selected or, more specifically, used. The objective of said filter medium is to filter particles or, more specifically, substances out of the fluid flow 14 with the aid of the processing unit 10. For example, the filter medium 16 may be a virus filter, a sterile filter, a depth filter or a membrane adsorber. The filter medium 16 is fashioned preferably as a filter mat or, more specifically, a filter membrane layer (or layers). In a preferred embodiment the filter medium 16 may consist of a plurality of layers. The filter medium 16 is arranged more or less in the vertical direction VR in the processing housing 12. In the processing housing 12 the filter medium 16 separates a filtrate side 18 from a retentate side 20. The filter medium 16 is fluidically permeable, where in this case filter medium-specific substances cannot pass through the filter medium 16. Since the fluid flow 14 is directed, as intended, from the retentate side 20 to the filtrate side 18, these filter medium-specific substances remain on the retentate side 20 and/or in the filter medium 16, but do not largely reach the filtrate side 18 of the processing unit 10. A fluid pressure difference prevails between the retentate side 20 and the filtrate side 18 as a function of the fluid pressure applied and/or the permeability of the filter medium 16.

At a preferably upper end 22 of the processing housing 12 there is at least one inflow channel 24, which extends preferably in a substantially horizontal direction HR and feeds the processing unit 10 with the medium to be filtered. As indicated in FIGS. 1A-1E with the aid of an arrow, the fluid flow 14 flows through the inflow channel 24 into the processing housing 12. In FIGS. 1A-1E, this means that a fluid flow 14 flows from the left into the processing housing 12. Then at least one portion of the fluid flow 14 flows from the retentate side 20 through the filter medium 16 to the filtrate side 18. If the processing unit 10 is connected in parallel to an additional processing unit (not shown here), then another portion of the fluid flow 14 flows directly to the additional processing unit without passing through the filter medium 16. This means that this portion of the fluid flow 14 flows into the inflow channel 24 of the additional processing unit (not shown). Then the fluid flow 14, which has passed through the filter medium 16 ("filtrate"), flows into an outflow channel 26 at the preferably lower end 28 of the processing housing 12 and flows from there out of the processing housing 12. Similarly the outflow channel 26 extends preferably in a more or less horizontal direction HR in the processing housing 12. Then the filtrate, leaving the processing housing 12, can flow into the outflow channel 26 of an additional processing unit (parallel circuit) (not shown here) and/or flow for further processing into the inflow channel 24 of the additional processing unit (series circuit).

Figure 1B:
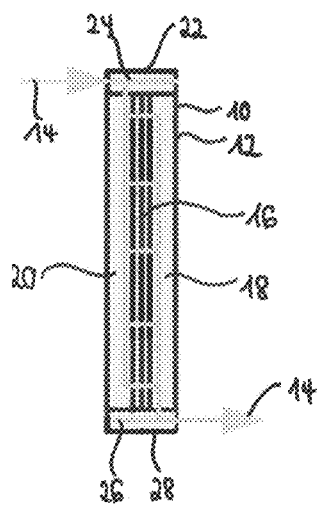

FIG. 1B shows the processing unit 10 from FIG. 1A, which differs from the unit in FIG. 1A only in that the filter medium 16 is configured as a multilayer structure.

Figure 1C:
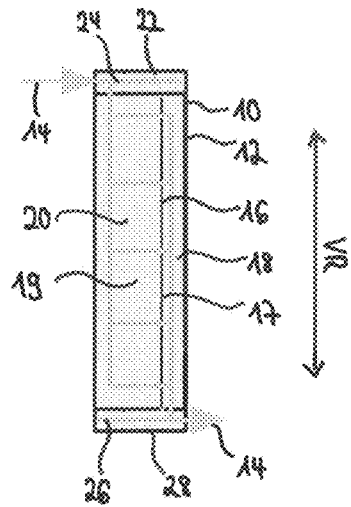

FIG. 1C shows a processing unit 10, which is configured, in principle, in a manner similar to the processing unit 10 from FIG. 1A, but differs in the manner of filtration. Therefore, only those parts of the processing unit 10 from FIG. 1C that differ from the processing unit 10 from FIG. 1A are described below.

In particular, the processing unit from FIG. 1C is designed for precoat filtration. For this purpose the filter medium 16 is configured as a precoat filter. In this embodiment the filter medium 16 comprises a filter support 17, which is arranged preferably in the vertical direction VR in the processing housing 12 and which is embodied to be relatively coarse. The precoat agent is usually mixed with the fluid before being introduced into the filter. In this way the construction of a filter cake (not shown here) is made possible. The filter support 17 is selected in such a way that at least one filter aid is retained. In order to provide sufficient space for the filter cake in the processing housing 12, an empty space 19 is formed on the retentate side 20.

Figure 1D:
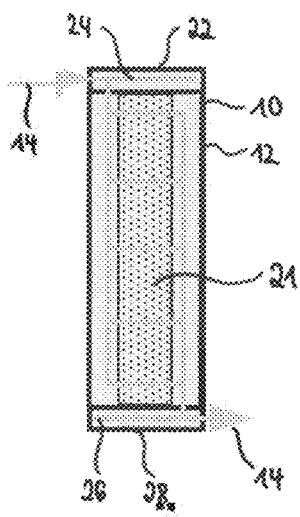

FIG. 1D shows an additional processing unit 10, which is constructed in a manner similar to the processing unit 10 from FIG. 1A, but has a bulk material 21, instead of a filter medium 16. In particular, the bulk material 21 can be gels or activated carbon, so that the processing unit 10 from FIG. 1C is suitable for chromatography.

In the context of chromatography, mixtures of substances can be separated. In this case the bulk material 21 serves as a stationary phase, which is arranged immovably in the processing unit 10. A mixture of substances is transported to the stationary phase with the aid of a mobile phase (for example, water). On account of the stationary phase interacting with individual substances in the mobile phase, the throughflow time of the corresponding substance can be delayed by the processing unit 10, so that a separation of substances is made possible.

Figure 1E:
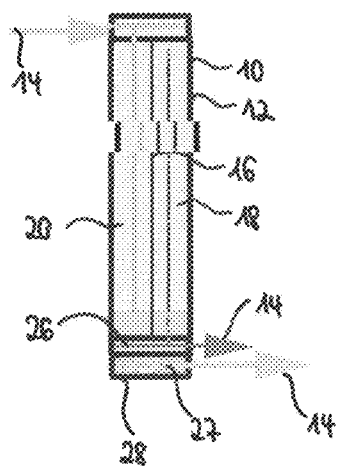

FIG. 1E shows an additional processing unit 10, which is also constructed in a manner similar to the processing unit 10 from FIG. 1A, but differs in that a second outflow channel 27 is provided. As a result, this processing unit 10 is suitable for tangential flow filtration or crossflow filtration. In this case a suspension to be filtered is pumped at a high speed parallel to the filter medium 16; and the filtrate is drawn off transversely to the direction of flow. Then the filtrate can be discharged through one of the outflow channels 26. That portion of the fluid flow 14 that does not pass through the filter medium 16, i.e., the retentate, can be discharged out of the processing unit 10 through the second outflow channel 27. Depending on the requirement, the filtrate or the retentate from the crossflow filtration can be further processed as part of the processing system, described in the following.

Figure 2A:
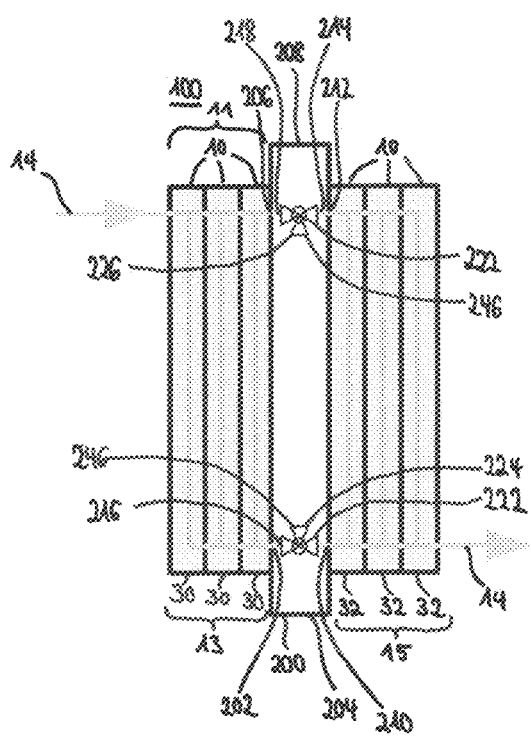
FIG. 2A shows a processing system with two processing unit groups in accordance with one embodiment, where said processing unit groups are connected in parallel with the aid of an adapter plate.
Figure 2B:
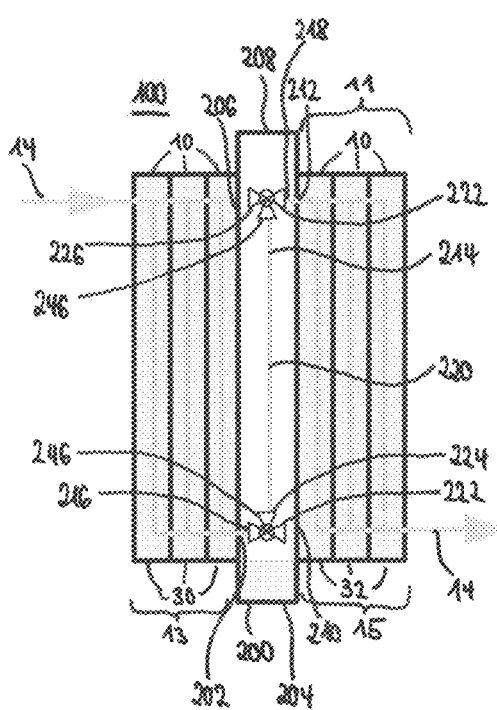
FIG. 2B shows the processing system from FIG. 2A), in which two processing unit groups are connected in series with the aid of the adapter plate.

FIGS. 2A and 2B show respective processing systems 100 with a plurality of processing units 10, which are described in FIGS. 1A to 1E; said processing units 10 are coupled directly to one another and form a processing unit group 11. As shown in FIGS. 2A and 2B, the processing systems 100 each respectively comprise a first processing unit group 13 and a second processing unit group 15, both of which are coupled with the aid of an adapter plate 200 in accordance with one embodiment of the invention. The processing units 10, which are directly coupled in FIGS. 2A and 2B, are shown as units that are connected in parallel, but can also be connected in series. The two processing unit groups 11, which are coupled with the aid of the adapter plate 200, can be connected both in parallel (see FIG. 2A) and in series (see FIG. 2B) with the adapter plate 200, or, alternatively, can be switched between these connecting modes with the adapter plate 200. This takes place in a simple manner and without structural changes in the processing system 100 via one or more deflection elements that are integrated in the adapter plate 200 (or, alternatively, provided on the adapter plate 200), as described below. By simply switching the one or more deflection elements, it is possible to switch between a parallel and serial connection of the processing unit groups 11. FIG. 2A shows a parallel connection of the processing unit groups 11, which are coupled via the adapter plate 200. FIG. 2B shows a serial connection of the two processing unit groups 11, which are coupled through the adapter plates 200. Although FIGS. 2A and 2B show processing unit groups 11 that are coupled through the adapter plate 200, the adapter plate 200 may also be used to couple only one processing unit 10 to a processing unit group 11 or two individual processing units 10 to one another.

The adapter plate 200 is configured preferably in a substantially plate-shaped manner and can be traversed by a fluid flow 14. The adapter plate 200 is embodied preferably as a disposable component with material properties that are selected preferably in such a way that a sterilization method, such as, for example, gamma irradiation, autoclaving, a perfusion with gas, such as ethylene oxide, and/or hot steam, can be applied. In particular, the adapter plate can be made of plastic. Processing units 10, which are arranged upstream of an adapter plate 200 in the direction of flow, are referred to as the first processing units 30, while processing units 10, which are arranged downstream of an adapter plate 200 in the direction of flow, are referred to as the second processing units 32. In other words, the first processing unit group 13 comprises first processing units 30; and the second processing unit group 15 comprises second processing units 32, as shown in FIGS. 2A) and 2B). The adapter plate 200 is arranged between the first processing unit group 13 and the second processing unit group 15 and fluidically connects the latter. The adapter plate 200 comprises at least one inlet opening, through which the fluid flow 14 can flow into the adapter plate 200. As shown in FIG. 2A, the adapter plate 200 has two inlet openings, in particular, a first inlet opening 202 at the preferably lower end 204 of the adapter plate 200, which is coupled to the outflow channel 26 of the first processing unit 30, which is arranged directly upstream of the adapter plate 200, and a second inlet opening 206 at the preferably upper end 208 of the adapter plate 200, which is coupled to the inflow channel 24 of this first processing unit 30. In other words, a fluid flow 14 can stream or, more specifically, flow from said first processing unit 30 through the first and second inlet openings 202 and 206, respectively, into the adapter plate 200. Furthermore, the adapter plate 200 has at least one outlet opening, through which the fluid flow 14 can exit the adapter plate 200. As shown in FIG. 2A), the adapter plate 200 has two outlet openings, in particular, a first outlet opening 210, which is arranged preferably on or, alternatively, near a lower end 204 of the adapter plate 200 and is or rather can be coupled to the outflow channel 26 of the second processing unit 32, which is arranged directly downstream of the adapter plate 200; and a second outlet opening 212, which is arranged preferably on or, alternatively, near an upper end 208 of the adapter plate 200 and is or rather can be coupled to the inflow channel 24 of this second processing unit 32. At least one adapter channel 214, which fluidically connects the inlet and outlet openings to one another, extends within the adapter plate 200. In particular, the adapter channel 214 has a first channel region 216 that extends between the first inlet opening 202 and the first outlet opening 210. A second channel region 218 extends between the second inlet opening 206 and the second outlet opening 212. The first and second channel region 216 and 218, respectively, is fluidically connected via a connecting channel region 220.

As shown in FIGS. 2A and 2B, at least two deflection elements are arranged in the adapter channel 214. In particular, said deflection elements are valves 222. In a preferred embodiment a first valve 224 is arranged in the first channel region 216; and a second valve 226 is arranged in the second channel region 218. In a specific embodiment the valves 222 are configured as multiway valves 246, as described below with reference to FIGS. 3A and 3B.

The at least one first and second processing unit 30 and 32, respectively, can be identical in construction or different, in order to be able to carry out different types of processes. Preferably the first processing units 30 in the first processing unit group 13 and the second processing units 32 of the second processing unit group 15 are identical in construction. However, it is also feasible that the first processing units 30 and the second processing units 32 differ respectively from one another. For example, the at least one first processing unit 30 can be embodied as a depth filter, while the at least one second processing unit 32 can be embodied as a sterile filter.

Figure 2C:
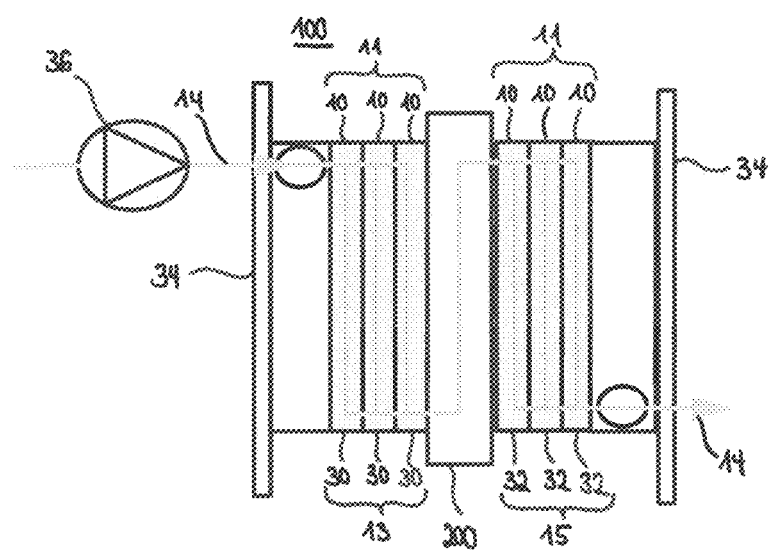
FIG. 2C shows the processing system from FIG. 2B, in which the individual processing units are held together by end brackets.

FIG. 2C shows the processing system 100 from FIG. 2B, in which the individual processing units 10 and the adapter plate 200 are held together with the aid of end brackets 34. In other words, at the entry point, at which the fluid flow 14 enters the processing system 100, and at the exit point, at which the fluid flow 14 exits the processing system 100, there is in each case an end bracket 34. This end bracket can be embodied preferably as a closure plate, so that the individual processing units 10 are held in a sandwich-like manner between these closure plates. Inlets and/or outlets may be part of the end bracket 34. In particular, however, an additional closure plate with corresponding connections can be introduced between an end bracket 34 and the respectively adjacent processing unit 10. Preferably the fluid flow 14 is pumped into the processing system 100 with the aid of a feed pump 36.

Figure 3A:
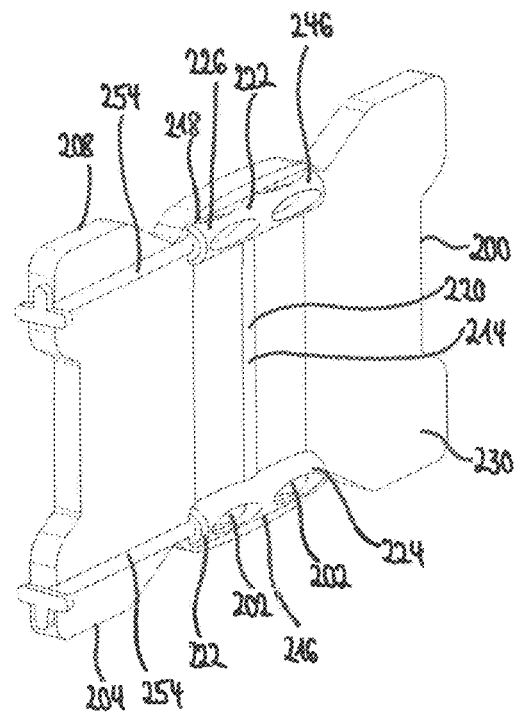
FIG. 3A shows a sectional view through an adapter plate from FIGS. 2A) and 2B) with a multiway valve.

FIG. 3A shows a sectional view through an adapter plate 200. As shown in FIG. 3A), the adapter plate 200 is formed preferably as a two-piece component and comprises a feed plate 230 and a discharge plate (not shown here). The plate of the adapter plate 200, in which the at least one inlet opening is arranged, is referred to as the feed plate 230. The plate of the adapter plate 200, in which the at least one outlet opening is arranged, is referred to as the discharge plate. The shape and/or size of the feed plate 230 and the discharge plate may be identical. In each case one multiway valve 246, which serves as a deflection element, is located in the first and/or second channel region 216 and 218, respectively. The multiway valve 246 comprises a valve tube 248, which extends at least partially in the first and second channel region 216 and 218, where it is mounted (in particular, so as to be turnable or rotatable). A displacement (in particular, rotation) can be carried out by hand with a handpiece 254 that protrudes from the adapter plate 200 (see FIGS. 3A and 3B) and/or can be carried out using an external control device (not shown).

At least two valve openings 252 are formed in a lateral surface 250 of the valve tube 248. Said two valve openings are arranged so as to be offset from one another in relation to the direction of displacement (in particular, the direction of rotation) in such a way that a first fluid flow or a second fluid flow is made possible in a first position of the valve tube 248. That means, for example, that the first fluid flow enters the valve tube 248 by way of the first inlet opening 202 of the adapter plate 200 through a first valve opening 252 that overlaps at least partially the first inlet opening 202.

The second valve opening 252 overlaps at least partially the first outlet opening 210, so that the first fluid flow can flow out of the adapter plate 200 through the first outlet opening 210. This applies correspondingly to the second fluid flow and the second inlet and outlet openings 206 and 212, respectively. A fluid flow 14 through the connecting channel region 220 is blocked based on the position of the valve openings 252 in the respective channel regions. Since, however, the first and second fluid flow through the multiway valves 246 is permitted, the first and second processing unit 30 and 32, each being coupled directly to the adapter plate 200, is connected in parallel.

Figure 3B:
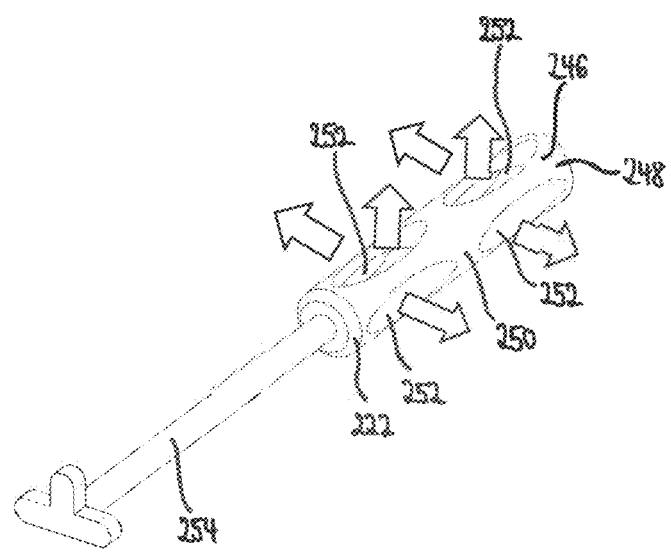
FIG. 3B shows the multiway valve from FIG. 3A)

However, the valve tubes 248 have preferably at least three valve openings 252, as shown in FIGS. 3A and 3B. These valve openings are arranged such that, in a first orientation (in particular, position of rotation) of the valve tube 248, at least two valve openings 252 are aligned such that the first and second fluid flows, described above, are permitted; and, thus, the first and second processing unit 30 and 32, each of which is coupled directly to the adapter plate, are connected in parallel. However, a fluid flow 14 through the connecting channel region 220 is prevented, since no valve opening 252 overlaps at least partially the connecting channel region 220.

However, as a result of the arrangement of the at least three valve openings 252, in a second orientation (in particular, the position of rotation) of the respective valve tube 248, either the passage to an inlet opening or to an outlet opening is blocked, while access to the connecting channel region 220 is permitted. This arrangement allows the first and second processing unit 30 and 32, respectively, to be connected in series.

In other words, in a serial connection the multiway valves 246 are oriented in such a way that a fluid flow 14 can enter the first valve tube 248 through the first inlet opening 202 of the adapter plate 200 and through a valve opening 252, which overlaps at least partially the first inlet opening 202. The fluid flow 14 can flow into the connecting channel region 220 through a valve opening 252, which overlaps at least partially the connecting channel region 220. The passage to the first outlet opening 210 is blocked by the valve tube 248, since no valve opening 252 overlaps the first outlet opening 210. Subsequently, the fluid flow 14 can flow into the second valve tube 248 through a valve opening 252 of the second valve tube 248, where said valve opening overlaps at least partially the connecting channel region 220. The fluid flow 14 can flow out of the adapter plate 200 through a valve opening 252 in the second valve tube 248, where said valve opening overlaps at least partially the second outlet opening 212 of the adapter plate 200. The passage to the second inlet opening 206 is blocked by the valve tube 248, since no valve opening 252 overlaps the second inlet opening 206.

Thus, it is possible to switch between a serial and parallel connection of two processing units 10 or processing unit groups 11 in a simple manner and without structural retrofitting measures. In particular, the adapter plate 200 is configured as a compact component, so that the processing system 100 has a small space requirement. The valves 222 can be designed as inexpensive disposable components. Possible applications can be: switching for tangential flow filtration from standard operation to single pass, switching between parallel and series connected chromatography units, for example, for the serial combination of different chromatography media or for improving the capacity utilization.

Figure 4:
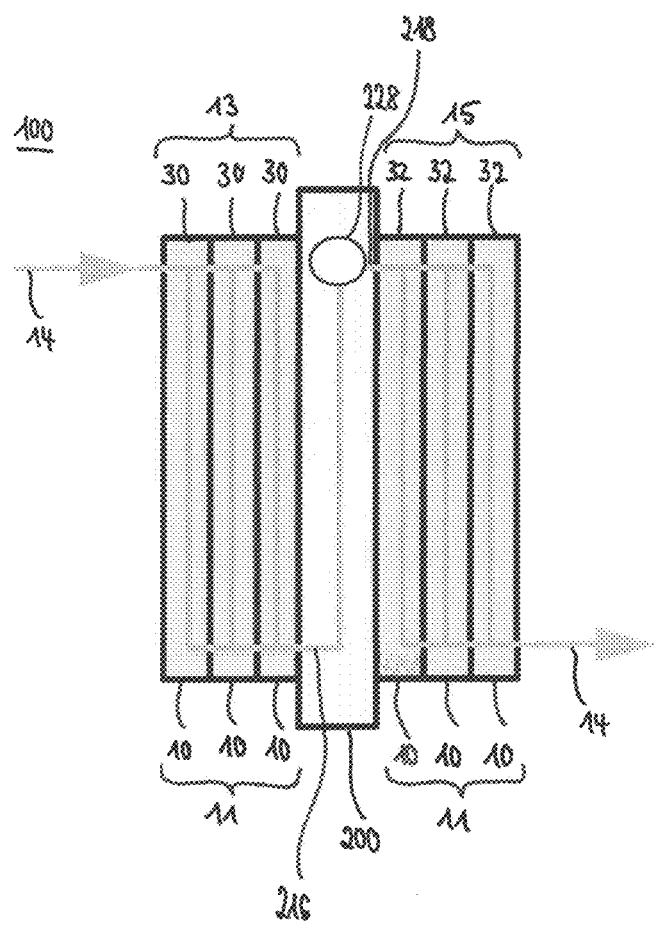
FIG. 4 shows a processing system with an adapter plate in accordance with a further embodiment, in which a sensor is integrated.

FIG. 4 shows an embodiment of a processing system 100, in which at least one sensor 228 is arranged in or, alternatively, on the adapter plate 200. In this case this sensor 228 is configured so that, for example, the pressure, the volume flow, the UV value, the pH value, the turbidity and/or the viscosity of the fluid flow 14 can be measured. The measured values can be used in turn to control the filtration process in an open loop or closed loop manner. For this purpose the measured values can be transmitted to an external control unit (not shown). The sensor 228 can be fashioned as an inexpensive disposable component.

In this case the illustrated adapter plate 200 couples the first and second processing unit group 13 and 15 serially. However, it is also possible to use sensors 228 when two processing unit groups 11 are connected in parallel. However, in this case it is necessary for the sensor(s) 228 to be arranged in or on the first and/or second channel region 216 and 218, respectively, in order to be able to make contact with the fluid flow 14. If the first and second processing unit groups 13 and 15, respectively, are connected in series, then the sensor 228 can also be arranged in or, alternatively, on the connecting channel region 220.

Figure 5A:
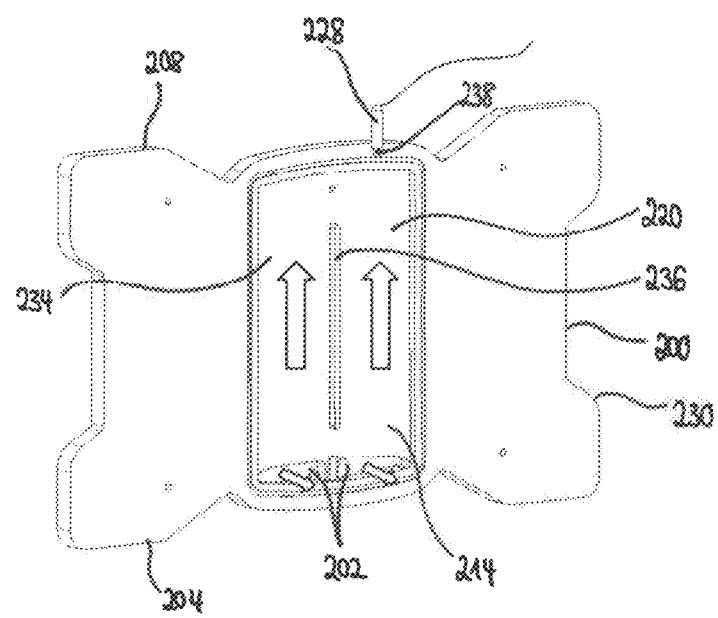
FIG. 5A shows a sectional view of a two-piece adapter plate with one sensor in accordance with a further embodiment.
Figure 5B:
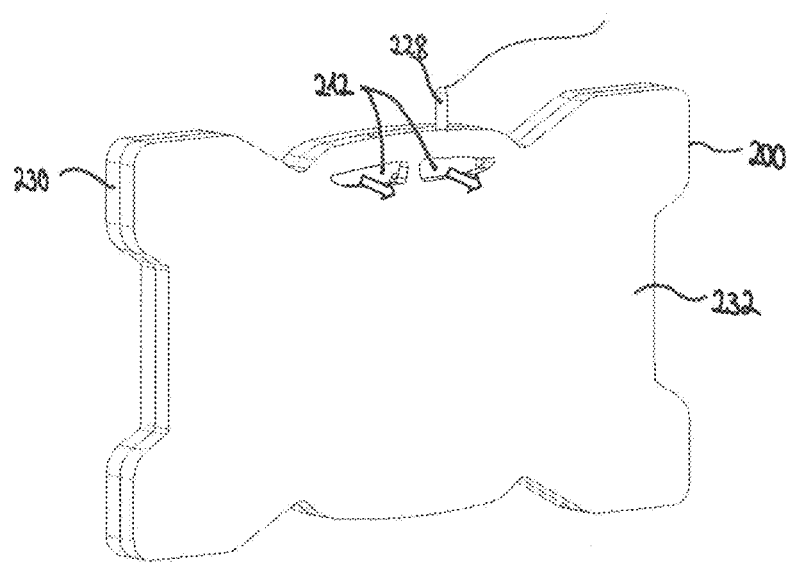
FIG. 5B shows a perspective view of the adapter plate from FIG. 5A)

FIGS. 5A and 5B show a preferred embodiment of an adapter plate 200, in which at least one sensor 228 is integrated. As shown in FIG. 5B, the adapter plate 200 is also configured preferably as a two-piece component or, alternatively, as a multi-piece component. The feed plate 230 comprises the at least one first inlet opening 202, preferably at the lower end 204 of the adapter plate 200. As shown in FIG. 5A, the feed plate 230 comprises two first inlet openings 202. However, said feed plate does not have any second inlet opening(s) 206. Since the illustrated adapter plate 200 is intended to permit only a serial connection between two processing units 10, they are, however, not absolutely necessary. For a parallel connection at least one second inlet opening 206, preferably at the upper end 208 of the adapter plate 200, could be formed in the feed plate 230.

As further shown in FIG. 5B, the discharge plate 232 comprises at least one second outlet opening 212. With respect to the specific case in FIG. 5B, the discharge plate 232 has two second outlet openings 212. Should a parallel connection between two processing units 10 be desired, then the discharge plate 232 can additionally have at least one first outlet opening 210. The feed and discharge plate 230 and 232, respectively, can be screwed and/or adhesively bonded and/or welded and/or snap locked to one another.

A corresponding channel recess 234 can be formed in the feed and/or discharge plate 230 and 232, respectively. When both the feed plate and the discharge plate 230 and 232, respectively, are assembled, an adapter channel 214 is formed in such a way that it makes it possible for a fluid flow 14 to flow through the adapter plate 200. Preferably at least one flow web 236 is formed in the connecting channel region 220 of the adapter channel 214. Said flow web extends preferably more or less in the direction of flow of the fluid flow 14 and helps to direct the fluid flow 14 in an improved manner. The sensor 228 may be integrated in the feed plates and/or discharge plates 230 and 232, respectively, and may project into the adapter channel 214 so that a measuring element of the sensor 228 can come into contact with the fluid flow 14. Preferably the adapter channel 214 comprises at least in certain areas a connecting channel 238 to the sensor 228. This connecting channel 238 may be at least in certain areas a recess in the adapter channel 214, into which the sensor 228 projects at least partially.

Figure 6A:
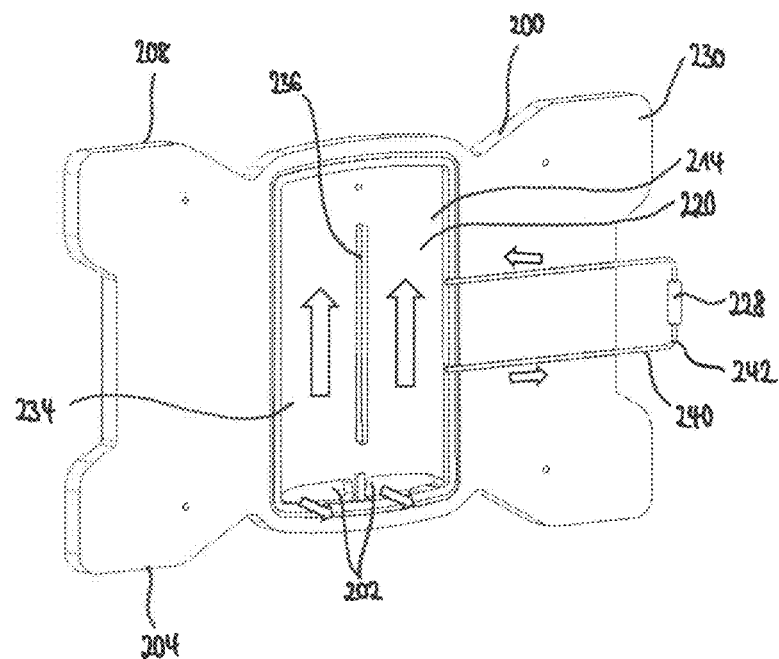
FIG. 6A shows a sectional view of an adapter plate in accordance with another embodiment with an auxiliary branch, in which a sensor is integrated.
Figure 6B:
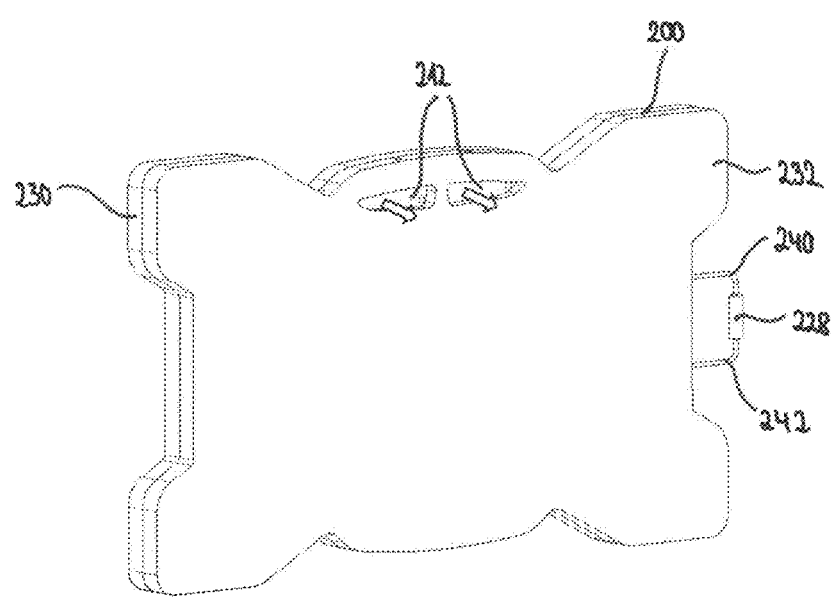
FIG. 6B shows a perspective view of the adapter plate from FIG. 6A)

FIGS. 6A and 6B show the adapter plate 200 from FIGS. 5A) and 5B). However, in this embodiment the sensor 228 is not arranged in or on the adapter channel 214, but rather in or, alternatively, on an auxiliary branch 240. The auxiliary branch 240 is a branch of the adapter channel 214, into which at least one portion of the fluid flow 14 is diverted. This portion of the fluid flow 14 flows out of the adapter channel 214 at least for a certain period of time, in order to be fed back again, preferably later, into the adapter channel 214.

The auxiliary branch 240 can be used to branch off small quantities of the fluid flow 14 for corresponding measurements. The auxiliary branch 240 can be formed with the aid of a separate channel element 242, which is integrated at least partially in the adapter plate 200. As shown in FIGS. 6A) and 6B), one portion of the auxiliary branch 240 may protrude from the adapter plate 200. As a result, in particular, the sensor 228 can also be arranged outside the adapter plate 200. However, this arrangement is also covered by the description "arranged on the adapter channel 214".

Figure 7A:
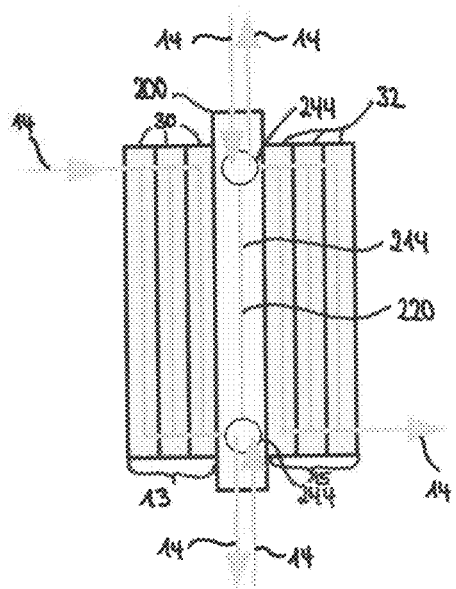
FIG. 7A shows a processing system with an adapter plate in accordance with a further embodiment, which has two auxiliary outputs and inputs.

FIG. 7A shows a processing system 100 with a first and second processing unit group 13 and 15, respectively, wherein the two processing unit groups are coupled via an adapter plate 200. In the illustrated embodiment the coupled processing unit groups 11 are connected in series through the adapter plate 200, but it is also possible to connect the two processing unit groups 11 in parallel in accordance with the other embodiments, described above.

In accordance with FIG. 7A, at least one auxiliary output and/or auxiliary input 244 can be formed in the adapter plate 200. At least one portion of the fluid flow 14 can be removed from or, more specifically, can flow out of the adapter channel 214 through an auxiliary output. The removed fluid flow 14 can flow back into the adapter channel 214 through an auxiliary input; or access to the adapter channel 214 can be ensured. The use of at least one auxiliary output or auxiliary input permits, for example, the external connection of a pump, an integrity test on different processing units 10 of the processing system 100, the discharge of the fluid out of the first or additional upstream processing units 30 for intermediate buffering or for further processing, venting and/or sampling. In particular, at least one diafiltration medium and/or other reagents can be added through an auxiliary input. FIG. 7A shows an adapter plate 200 with two auxiliary outputs and auxiliary inputs 244. Possible connections to an auxiliary output and auxiliary input 244 could be triclamps or sterile connectors.

Figure 7B:
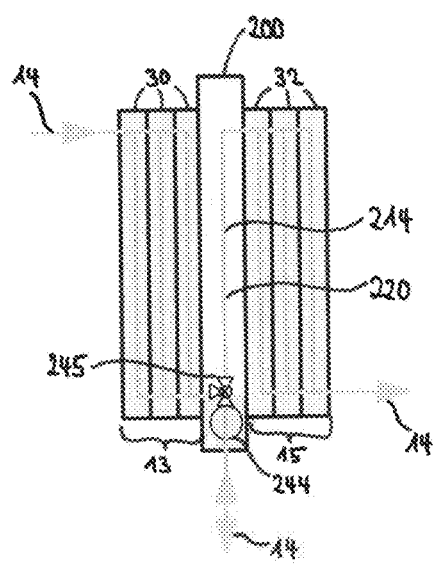
FIG. 7B shows the processing system from FIG. 7A) with one auxiliary output and one auxiliary valve.

FIG. 7B shows the processing system 100 from FIG. 7A, but with only one auxiliary output or input 244. In this case the first and second processing unit group 13 and 15, respectively, are also connected in series; in particular, it is a serial connection of chromatography steps. In this embodiment the at least one first processing unit 30 is preferably a bind and elute unit. A chromatography step can be, for example, affinity chromatography with protein A ligand coupled to membranes (membrane adsorbers) or gels. In order to not contaminate the at least one second processing unit 32, at least one auxiliary output 244 can be provided in the adapter plate 200, so that a fluid flow 14 can flow out of the outflow channel 26 of the first processing unit 30, which is coupled directly to the adapter plate 200, through the auxiliary output 244. In particular, various buffers and washing solutions can be discharged through the auxiliary output 244.

Preferably an auxiliary valve 245 is arranged on the auxiliary output 244, in order to deflect the fluid flow 14 between the auxiliary output 244 and the second processing unit 32, which is coupled directly to the adapter plate 200.

A possible sequence of the process in the processing system 100 of FIG. 7B could be:
(1) equilibration: A buffer solution is used to clean the chromatography medium and to bring it into the desired state of equilibrium; the emerging buffer solution from the first processing unit 30, which is coupled directly to the adapter plate 200, is discharged through the auxiliary output 244 of the adapter plate 200.
(2) loading with the fluid flow 14 to be processed: The target molecule from the fluid flow 14 is bound in the chromatography material of the first processing unit group 13; the remaining liquid with impurities emerges from the first processing unit 30, which is coupled directly to the adapter plate 200, through the auxiliary output 244 of the adapter plate 200.
(3) washing: Buffer solution is used to purge remaining impurities from the first processing unit group 13; the emerging buffer solution with the impurities is discharged through the auxiliary output 244 of the adapter plate 200.
(4) elution: With an additional buffer solution the target molecule is dissolved again by the chromatography material of the first processing unit group 13 and can be passed directly into the second processing unit group 15 through the second processing unit 32, which is coupled directly to the adapter plate 200 (at the same time the auxiliary output 244 is closed); in this case the second processing units 32 are chromatography units that can bind additional impurities (flow-through polishing) or the target molecule (bind and elute), depending on the process applied.

(5) cleaning/regenerating/decontaminating: the chromatography material of the first processing unit group 13 is treated with an additional solution; the emerging solution with the impurities is discharged through the auxiliary output 244 of the adapter plate 200.

The auxiliary input and output 244 can also be used to carry out at least one of the steps, described in the previous sequence, separately from the first processing unit group 13. In so doing, the adapter plate 200 is used to feed in corresponding solutions, in order to treat at least one second processing unit 32.

The described sequence of steps can be expanded or reduced, as desired.

Figure 7C:
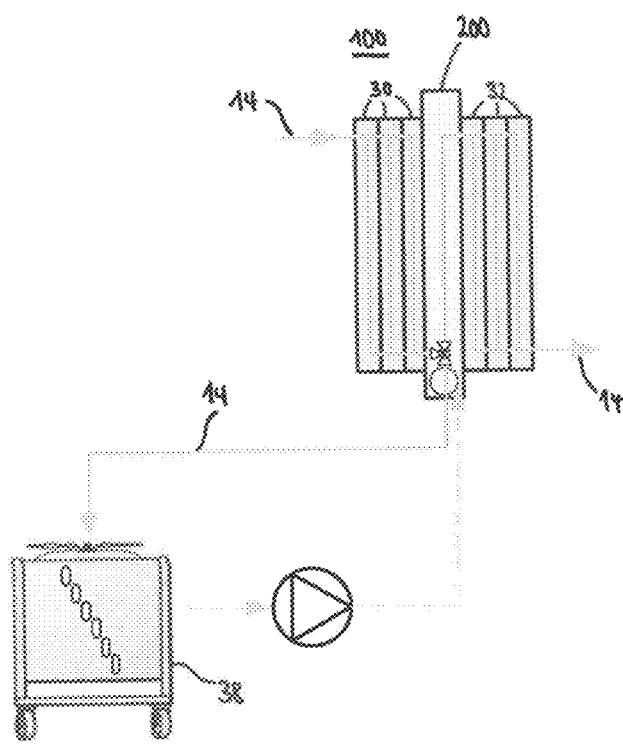
FIG. 7C shows the processing system from FIG. 7B) with an external mixing tank.

In step (4), the target molecule for intermediate storage and/or for further processing (for example, viral inactivation at low pH values in a mixing tank 38) can also be discharged through the auxiliary output 244, as shown in FIG. 7C. At a later stage said target molecule is then fed back to the second processing unit group 15.

Figure 8A:
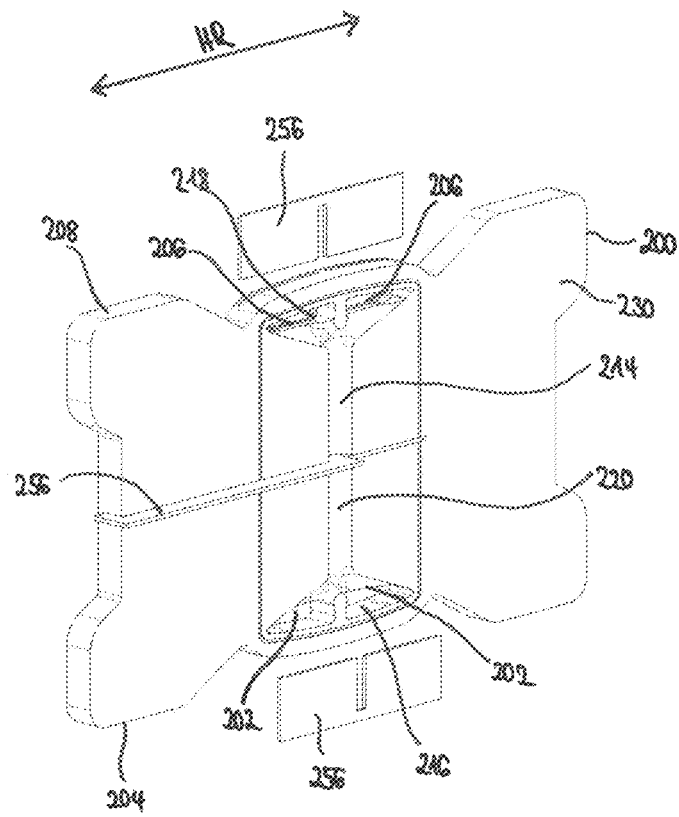
FIG. 8A shows a sectional view through a two-piece adapter plate with displaceable deflection elements, wherein the connecting channel region is blocked by the deflection element.
Figure 8B:
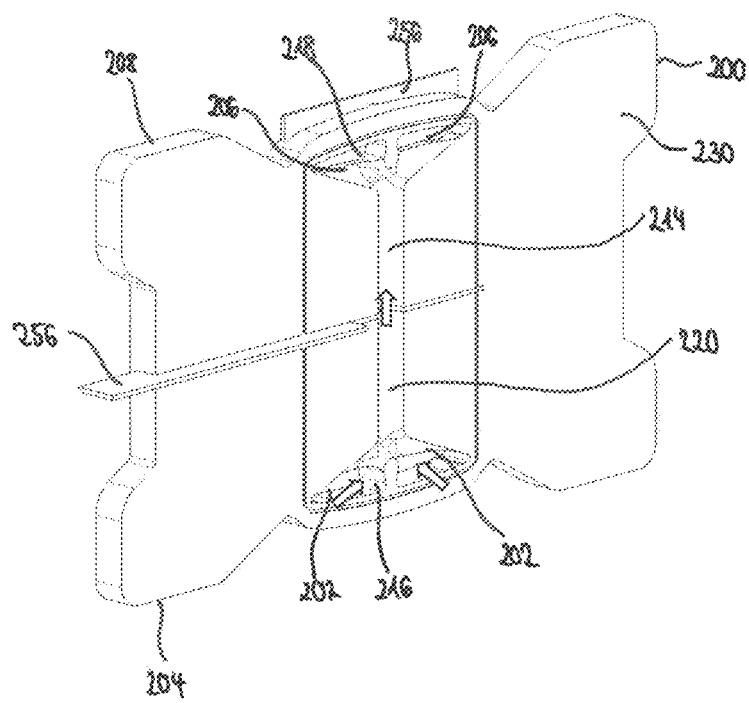
FIG. 8B shows the adapter plate from FIG. 8A), wherein a fluid flow through the connecting channel region is released by the deflection element.

FIGS. 8A and 8B show another embodiment of a two-piece adapter plate 200 with at least one deflection element. In particular, the deflection element, as shown in this embodiment, is mounted displaceably in the adapter plate 200. In particular, the deflection element (hereinafter referred to as a "closure element 256") is mounted in the adapter plate 200 so as to be displaceable or, more specifically, shiftable in such a way that in a first position of the closure element 256, the closure element 256 projects at least partially into the adapter channel 214, in order to block a fluid flow 14 through the adapter channel 214 completely or at least partially (see FIG. 8A). In a second position of the closure element 256 the closure element 256 does not project into the adapter channel 214, so that a fluid flow 14 can flow substantially unimpeded.

The closure element 256 is configured preferably as a plate. A correspondingly configured slot or, more specifically, recess is formed for the corresponding closure element 256 in the adapter plate 200; and the closure element 256 is mounted so as to be displaceable or, more specifically, shiftable in this slot. It is possible to provide a closure element 256 that is arranged in such a way that a fluid flow 14 through the connecting channel region 220 can be blocked. For this purpose the closure element 256 can be pushed or, more specifically, inserted into the connecting channel region 220 preferably in the horizontal direction HR.

Furthermore, in each case one closure element 256 can be provided, so that it can be pushed or, more specifically, inserted into the first and/or second channel region 216 and 218 respectively. This means that a closure element 256 can be pushed or, more specifically, inserted from above or from below into the respective channel region. In particular, a closure element 256 can be pushed into the first channel region 216 in such a way that the at least one first outlet opening 210 can be blocked by the closure element 256. The additional closure element 256 can be pushed into the second channel region 218 in such a way that the at least one second inlet opening 206 can be blocked by the closure element 256. In other words, the said closure elements 256 can be used to connect the first and second processing unit groups 13 and 15, respectively, or a first and second processing unit 30 and 32, respectively, in parallel or in series.

FIG. 8A shows a parallel connection between the processing units 10, in that one closure element 256 is pushed or rather inserted into the connecting channel region 220; and a fluid flow 14 through the connecting channel region 220 is blocked. FIG. 8B shows a serial connection between the processing units 10, in that closure elements 256 are pushed into the first and second channel region 216 and 218, respectively. However, the fluid flow 14 through the connecting channel region 220 is not blocked by a closure element 256.

The closure elements 256 can be manually displaced and/or shifted and/or can be pushed via an external controller (not shown) and a coupled motor (not shown).

Figure 9:
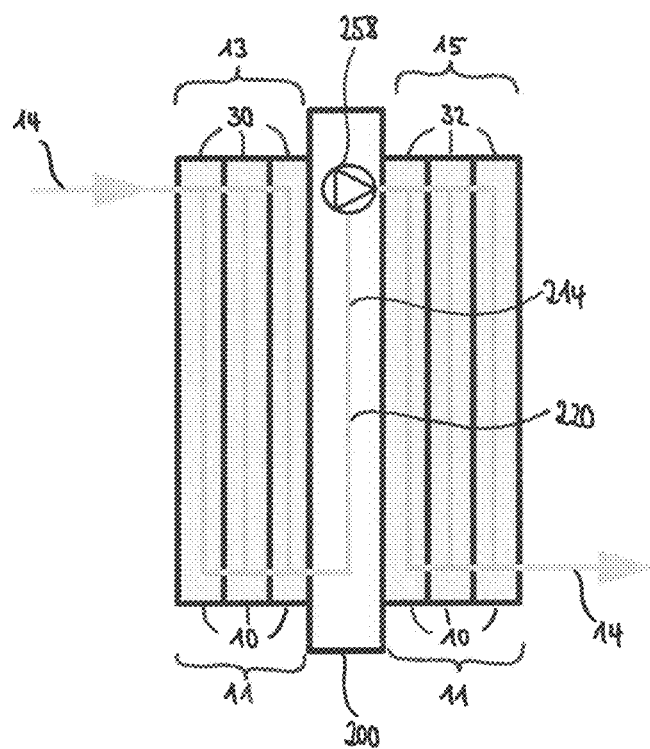
FIG. 9 shows a processing system with an adapter plate in accordance with a further embodiment, in which a pump is integrated.

FIG. 9 shows a processing system 100 with a first and second processing unit group 13 and 15, respectively. The first and second processing unit groups 13 and 15, respectively, are coupled through an adapter plate 200. At least one pump 258 is arranged in or, alternatively, on the adapter channel 214 of the adapter plate 200. Said pump can be used in a parallel connection of two processing unit groups 11, but is particularly advantageous in a serial connection, as shown in FIG. 9, since in this way, for example, a flow resistance can be overcome; and, thus, sufficient filtration performance can be achieved in the second processing unit group 15.

Furthermore, the pump 258 can be configured, in particular, as a positive displacement pump, in order to initiate a negative pressure in the first processing unit group 13 and to build up a desired filtration pressure in the second processing unit group 15. In particular, the pump 258 can be fashioned as an inexpensive disposable component.

Figure 10A:
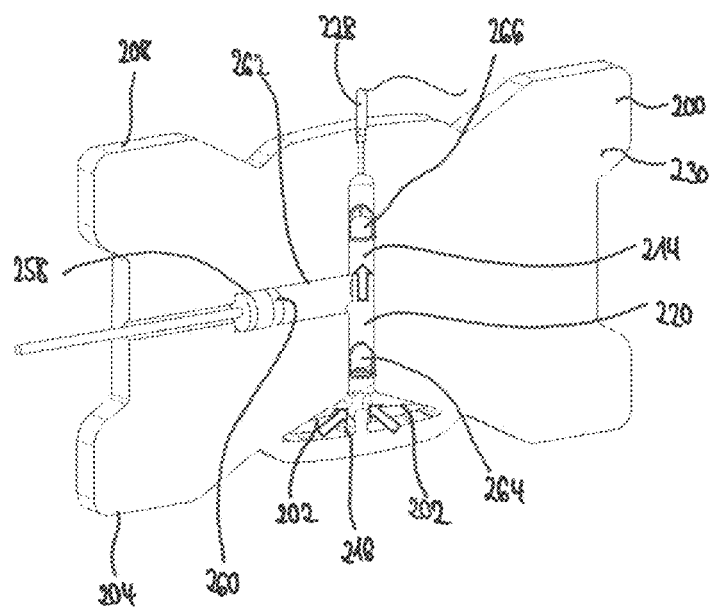
FIG. 10A shows a sectional view through an adapter plate with a piston pump in an intake position.
Figure 10B:
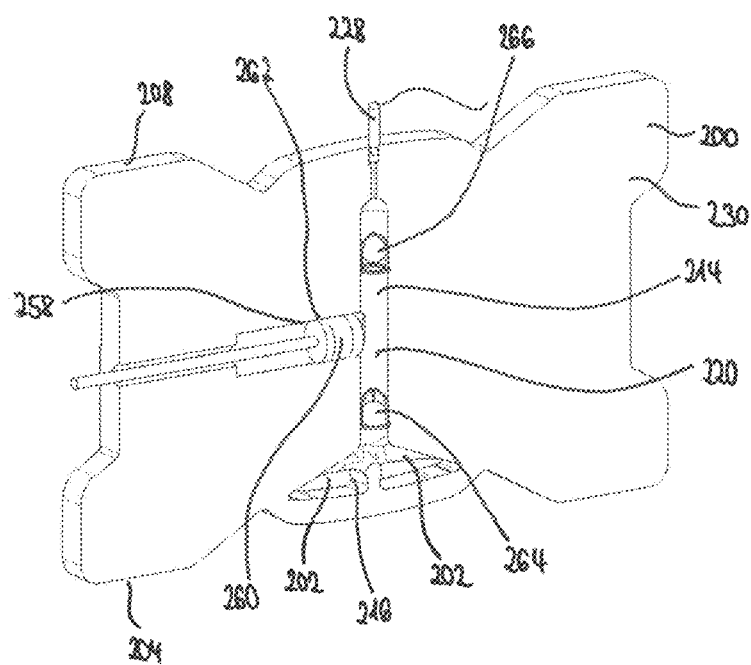
FIG. 10B shows a sectional view of the adapter plate from FIG. 10A) in a stroke position.

FIGS. 10A and 10B show a specific embodiment of an adapter plate 200 with a positive displacement pump, in particular, a piston pump. The pump 258 is arranged preferably in the connecting channel region 220 and comprises at least one piston 260, which is configured to carry out a stroke motion, i.e., a rectilinear (translatory) motion. For this purpose the piston 260 is mounted in a cylinder 262. In addition, the pump 258 has an inflow and an outflow, each of which can be closed by a valve.

In particular, one section in the connecting channel region 220 is separated or, more specifically, delimited in the direction of flow by an intake valve 264 and by an exhaust valve 266. The fluid may flow into this section through the intake valve 264 and may escape through the exhaust valve 266. The cylinder 262, in which the piston 260 is mounted and can perform a translatory motion therein, is arranged in such a way that the cylinder 262 is arranged on the connecting channel region 220 and is fluidically connected thereto. In particular, the cylinder 262 is arranged between the intake and exhaust valve 264 and 266, respectively, on the connecting channel region 220.

In a first cycle during suction, the piston 260 executes a rearward motion, i.e., a movement away from the connecting channel region 220. The intake valve 264 opens; and the fluid to be conveyed can flow into the connecting channel region 220 or, more specifically, the cylinder 262. In a second cycle during the conveying motion, the intake valve 264 closes; and the piston 260 moves in the direction of the connecting channel region 220. The exhaust valve 266 opens; and the medium to be conveyed is pushed out.

At least one sensor 228 is disposed preferably in the adapter channel 214, in order to monitor the fluid flow 14. For this purpose the sensor 228 can be arranged preferably downstream of the pump 258 in the direction of flow, in order, for example, to measure the fluid pressure or the fluid flow. This value can be used to regulate the pump 258 through an external control device.

Figure 11A:
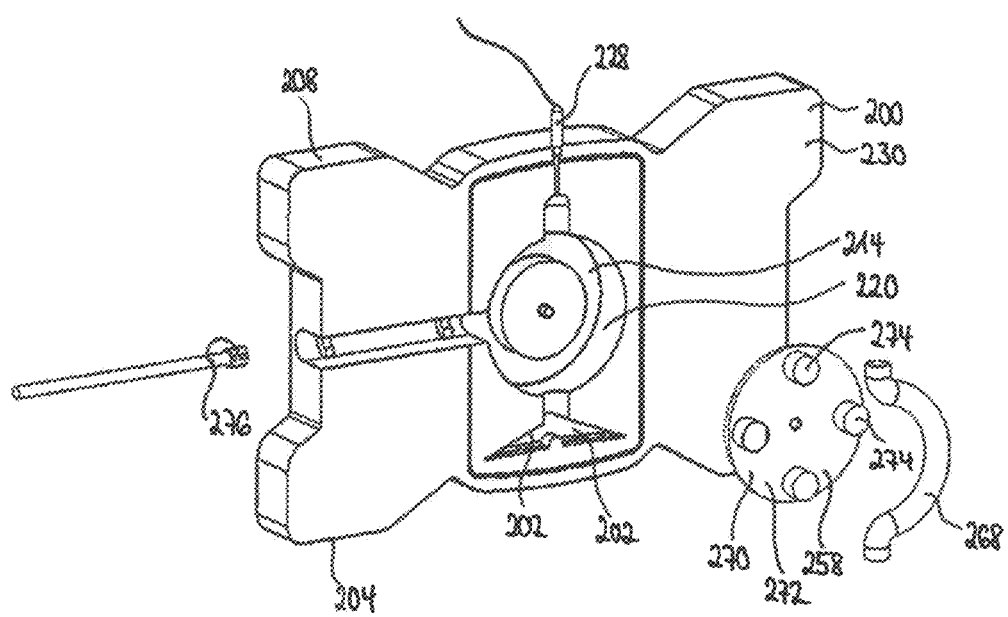
FIG. 11A shows an exploded view of an adapter plate with a peristaltic pump in accordance with a further embodiment.
Figure 11B:
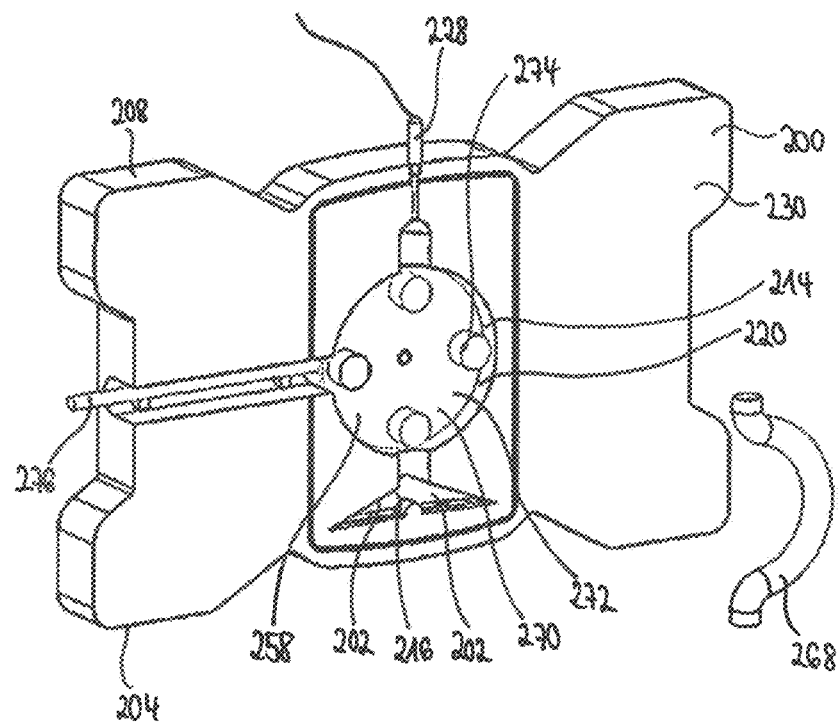
FIG. 11B shows a sectional view of the adapter plate from FIG. 11A)

Another possibility of a positive displacement pump is shown in FIGS. 11A and 11B. The pump 258, which is integrated in the adapter plate 200, is a peristaltic pump, which is arranged preferably in the connecting channel region 220 for the reasons already described above.

A peristaltic pump, also called a hose pump, is a positive displacement pump, in which the external mechanical deformation of a hose 268 causes the fluid to be conveyed to be forced through said hose. Therefore, in the present case the hose 268 constitutes a part of the connecting channel region 220, through which the fluid flows in the adapter plate 200. The region, in which the hose 268 is arranged, is circular; or, more specifically, the connecting channel region 220 widens in a curved manner. A rotor 270 is arranged in the circular section of the connecting channel region 220, where said rotor is rotatably mounted.

The rotor 270 is constructed preferably as a circular plate. At least one roller 274 and/or a sliding block is/are arranged on an upper side 272 of the rotor 270. The hose 268 rests at least in certain areas against a lateral surface of the circular section of the connecting channel region 220. The hose 268 can be clamped from the inside by the rollers 274 and/or sliding blocks by rotating the rotor 270. This results in a pinch point moving along the hose 268; and, as a result, propels the fluid to be conveyed forward. The rotor 270 can be rotated with a gear mechanism 276, as shown in FIGS. 11A and 11B. At least one sensor 228 may be arranged in the adapter plate 200 in a manner similar to the embodiment of FIGS. 10A and 10B.

Figure 12A:
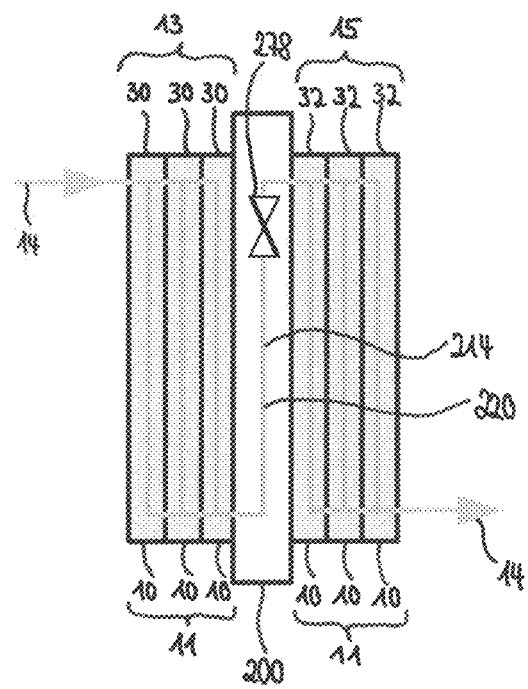
FIG. 12A shows a processing system with an adapter plate in accordance with a further embodiment, in which a flow limiter is integrated.

FIG. 12A) shows a processing system 100 with a first and second processing unit group 13 and 15, respectively, where both groups are coupled with an adapter plate 200. A flow limiter 278 is integrated in the adapter plate 200 of this embodiment. Said flow limiter can be used in an advantageous way to regulate the flow and/or pressure of the fluid flow 14. This aspect is particularly useful in the serial connection of two processing unit groups 11 or, more specifically, processing units 10, as shown in FIG. 12A).

Figure 12B:
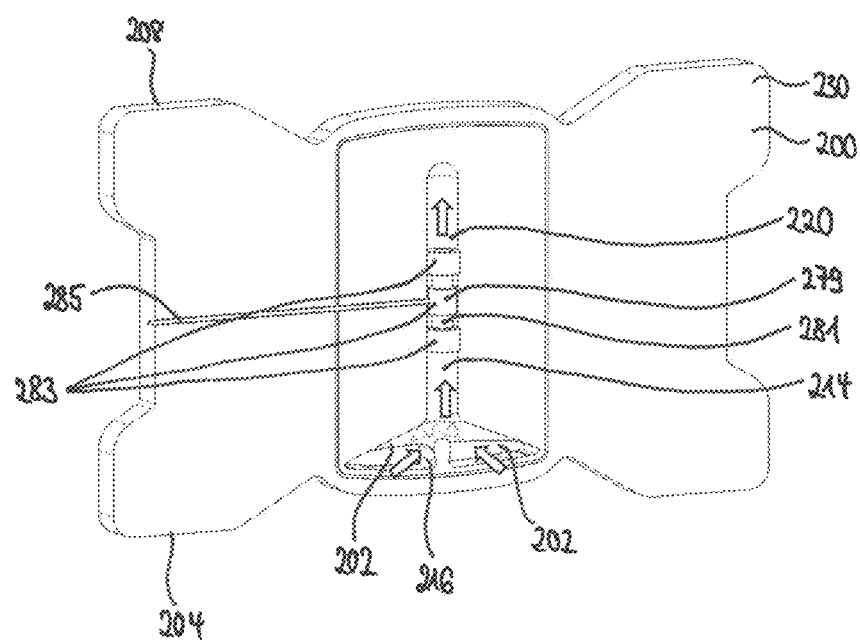
FIG. 12B shows a sectional view of the adapter plate from FIG. 12A)

FIG. 12B) shows the adapter plate 200 from FIG. 12A in a sectional view with a pinch valve as a flow limiter 278. For this purpose at least one flexible blocking element 279 is arranged, preferably at least in some areas, in the connecting channel region 220. The flexible blocking element 279 is configured in a channel-shaped manner so that in a first position the fluid flow 14 can flow unimpeded through the flexible blocking element 279. The blocking element 279 is d preferably as a hose element, in particular, as a silicone hose. As shown in FIG. 12B, the blocking element 279 can have on its outer lateral surface 281 at least one blocking lip 283, which is arranged circumferentially in the direction of rotation of the blocking element 279. In order to prevent or at least to limit a fluid flow 14 through the connecting channel region 220, the blocking element 279 can be squeezed at least in some areas, in order to reduce the cross sectional area of the throughflow channel (not visible here) with the blocking element 279 or to completely close the throughflow channel at least in some areas, so that a throughflow is completely eliminated. The squeezing process can take place mechanically using a tappet 285 which, as shown in FIG. 12B, is mounted in the adapter plate 200 in a translatory manner at least in some areas. A forward motion allows the tappet 285 to squeeze the blocking element 279. A rearward motion allows the tappet 285 to expand or completely release the throughflow channel again. The blocking element 279 is arranged preferably in the connecting channel region 220 in such a way that the outer lateral surface 281 of the blocking element 279 terminates with the connecting channel region 220 in a fluid-tight manner. Preferably the one blocking lip 283, which is arranged on the outer lateral surface 281 of the blocking element 279, helps to achieve this objective. In order to prevent fluid from flowing between the blocking element 279 and the connecting channel region 220 in a pinched position of the blocking element 279, preferably only a central subregion is squeezed in the pinched position of the blocking element 279.

As an alternative to a pinch valve, the flow limiter 278 may be formed by at least two small cruciform plates, which are arranged rotatably in the connecting channel region 220. The small cruciform plates have a common axis of rotation that corresponds to the direction of flow of the fluid flow 14. The plates lie preferably on top of one another. In a first position of the small plates, the cross arms are arranged in such a way that a throughflow of the fluid flow 14 between the cross arms is made possible. In a second position of the small plates the cross arms can be arranged in such a way that a throughflow is reduced or completely eliminated. The small plates can be embodied as small, stainless steel spring plates. In this case a pressure difference influences the position of the small plates in relation to one another. A decreasing differential pressure causes an increase in the opening; and a pressure increase correspondingly causes a reduction. In this way the amount of fluid, flowing through the adapter plate 200, can be kept constant.

Figure 13:
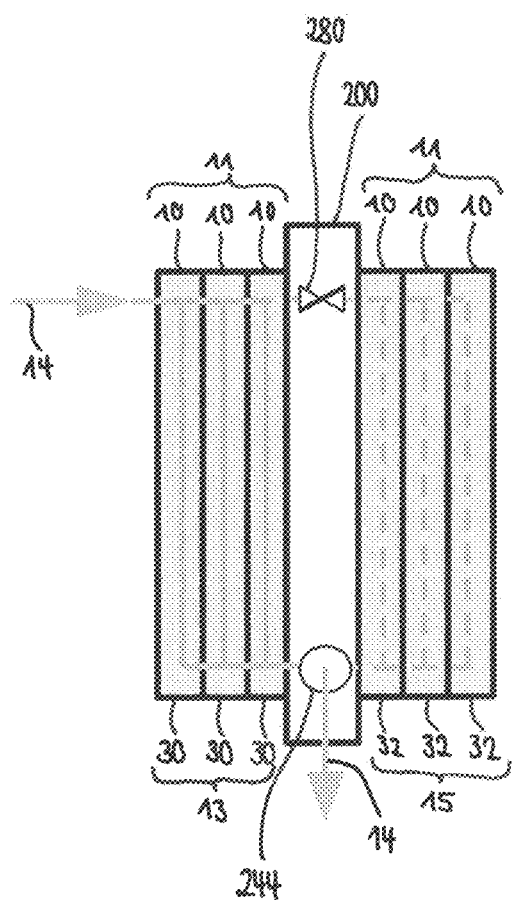
FIG. 13 shows a filter system with an adapter plate for one possible filter extension in accordance with an additional embodiment.

FIG. 13 shows an additional processing system 100 with a first and second processing unit group 13 and 15, respectively. An adapter plate 200, which is integrated in the processing system 100, is used to add at least one additional processing unit 10, in order to expand the filter area, as required. As shown in FIG. 13, the second processing unit group 15 can be added through the adapter plate 200. However, it is also possible to add only a second processing unit 32.

As shown in FIG. 13, at least one expansion valve 280 is integrated or rather provided preferably in the adapter plate 200. This expansion valve 280 is arranged preferably in or, alternatively, on the second channel region 218. Since in this embodiment the first and second processing unit groups 13 and 15, which are coupled through the adapter plate 200, are connected in parallel, a fluid flow 14 can flow out of the inflow channel 24 of the first processing unit 30, which is coupled directly to the adapter plate 200, to the inflow channel 24 of the second processing unit 32, which is coupled directly to the adapter plate 200, should an expansion of the filter area be desired. The expansion valve 280 can be configured as a self-regulating valve, such as, for example, a pressure relief valve, or as an externally controlled valve.

Furthermore, at least one auxiliary output 244, which is arranged preferably in or, alternatively, on the first channel region 216 of the adapter channel 214, can be formed in the adapter plate 200. In the event that the first and second processing unit groups 13 and 15, respectively, are not to be coupled to one another (i.e., no filter expansion), then the fluid flow 14 from the outflow channel 26 of the first processing unit 30, which is coupled directly to the adapter plate 200, can flow out of the processing system 100 through this auxiliary output 244. If, however, the first and second processing unit groups 13 and 15, respectively, are coupled to one another (i.e., a filter expansion takes place), then the fluid flow 14 from at least the outflow channel 26 of the second processing unit 32, which is coupled directly to the adapter plate 200, can also flow out through the auxiliary output 244 of the adapter plate 200. In this respect it should be noted that although the first outlet opening 210 is described in the rest of the description in such a way that a fluid can flow out of the adapter plate 200 into the outflow channel 26 of the second processing unit 32, the first outlet opening 210 does not have to be exclusively deflected for this one direction of flow. The first outlet opening 210 can also be used, as, for example, in FIG. 13, for a fluid (here filtrate) to be able to flow out of the outflow channel 26 of the second processing unit 32, which is coupled directly to the adapter plate 200, and then back again into the adapter plate 200, in order then to be able to flow out of the adapter plate 200 through the auxiliary output 244. In order to make such a direction of flow possible, a non-return valve can be arranged preferably on the first outlet opening 210.

During cell separation with depth filters, the filterable amount of solution varies until the filtration capacity has been reached, as a result of the various cell types, cell densities and filter properties. In this case the filter area can be expanded, as and when required, with an adapter plate 200, as described above. Thus, the filtration process does not have to be interrupted. Furthermore, unused processing units 10 could be used in a further filtration.

It should be noted that the embodiment of FIG. 13 has been described only with respect to a parallel connection between the first and second processing unit group 13 and 15, respectively. However, it is also feasible for the second processing unit group 15 to be connected in series to the first processing unit group 13. In this case, then, the expansion valve 280 could be arranged in any other region of the adapter channel 214.

Figure 14:
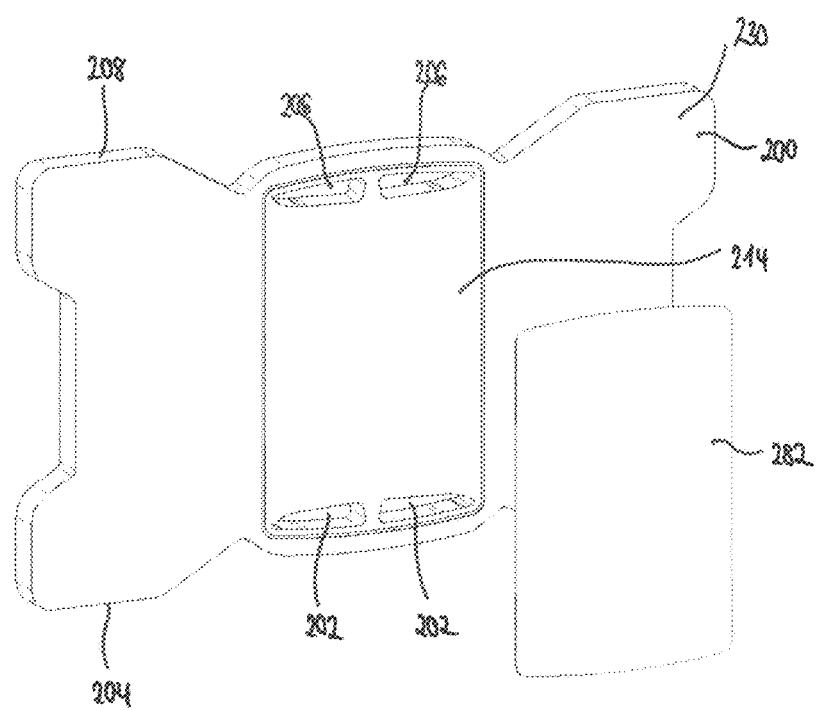
FIG. 14 shows a sectional view of an adapter plate in accordance with another embodiment with a rupture disk for pressure relief.

FIG. 14 shows a sectional view through an adapter plate 200 in accordance with another embodiment. At least one rupture pressure disk 282 is integrated or rather provided in this adapter plate 200, which is arranged at least in some areas in the region, in which the adapter channel 214 is located. The rupture pressure disk 282 can be made of stainless steel, graphite, silicone or plastic. It is advantageous to provide the rupture pressure disk 282 in the adapter plate 200, when high levels of pressure (for example, at pressure levels between 1 and 5 bar) are to be expected in the adapter plate 200. In a two-piece adapter plate 200, which has a feed plate 230 and a discharge plate 232, the rupture pressure disk 282 is arranged between these plates, so that a fluid flow 14 is blocked by the adapter plate 200. If, however, for example, the filter medium 16 of the first processing unit 30 is blocked, then the pressure rises; and the rupture pressure disk 282 bursts, so that a fluid flow 14 through the adapter plate 200 to the second processing unit 32 is ensured.

Additional comments about the embodiments, described above:

In various embodiments the adapter plate 200 is described for linking two processing unit groups 11 together. However, it should be noted that the descriptions also apply correspondingly to embodiments, in which only a first and/or second processing unit 30 and 32, respectively is/are provided.

In the processing systems 100 described, an adapter plate 200 is shown that couples two processing unit groups 11. However, it is possible for a plurality of adapter plates 200 to be contained in a processing system 100. Processing unit groups 11, which are coupled through an adapter plate 200, are always referred to herein as a first and second processing unit group 13 and 15, respectively; and the above description applies correspondingly to each linking of two processing unit groups 11. The same also applies to individual processing units 10, linked via an adapter plate 200, or individual processing units 10, which are linked to a processing unit group 11.

Furthermore, it should be noted that although the illustrated adapter plates 200 are embodied as a two-piece component, it is also feasible to embody them in one piece.

In the above description the focus is on the biopharmaceutical use of the processing systems 100 or, more specifically, adapter plates 200. However, it is also possible to transfer the principle, shown, to other processes, such as, for example, food production, chemical production processes, beverage filtration, fractionation of particles, waste water treatment and the like.

In particular, it should be noted that the adapter plate 200 in each of the described embodiments is coupled directly or, more specifically, without the interposition of further elements to a second processing unit 32. However, it is possible to connect the adapter plate 200 to the second processing unit 32 through a compatible connection, which is designed preferably so as to be sterile and/or dripless.

The adapter plate 200 can also be arranged upstream and/or downstream of the last processing unit 10 of a processing system 100. In particular, a filter cassette called "Sartoclear® Depth Filter Cassette" and/or a filter cassette of the "Sartoclear® DL series" and/or a filter cassette of the "Sartoclear® S series" by Sartorius Stedim Biotech GmbH can be used as one or more processing units 10.

The various embodiments of the processing systems 100 or, more specifically, adapter plates 200 have been described separately with reference to the individual figures. However, it should be noted that the individual embodiments or, more specifically, parts of the individual embodiments can be combined with one another. In order to avoid repetition, elements, which have already been described with respect to the individual embodiments, have not been described once again.

LIST OF REFERENCE NUMERALS AND CHARACTERS 10 processing unit
11 processing unit group
12 processing housing
13 first processing unit group
14 fluid flow
15 second processing unit group
16 filter medium
17 filter support
18 filtrate side
19 empty space
20 retentate side
21 bulk material
22 upper end of the processing housing
24 inflow channel
26 outflow channel
27 second outflow channel
28 lower end of the processing housing
30 first processing unit
32 second processing unit
34 end bracket
36 feed pump
38 mixing tank
100 processing system
200 adapter plate
202 first inlet opening
204 lower end of the adapter plate
206 second inlet opening
208 upper end of the adapter plate
210 first outlet opening
212 second outlet opening 214 adapter channel
216 first channel region
218 second channel region
220 connecting channel region
222 valve
224 first valve
226 second valve
228 sensor
230 feed plate
232 discharge plate
234 channel recess
236 flow web
238 connecting channel to the sensor
240 auxiliary branch
242 channel element
244 auxiliary output or auxiliary input
245 auxiliary valve
246 multiway valve
248 valve tube
250 lateral surface of the valve tube
252 valve opening
254 handpiece
256 closure element
258 pump
260 piston
262 cylinder
264 intake valve
266 exhaust valve
268 hose
270 rotor
272 upper side of the rotor plate
274 roller of the rotor
276 gear mechanism
278 flow limiter
279 flexible blocking element
280 expansion valve
281 outer lateral surface
282 rupture pressure disk
283 blocking lip
285 tappet
VR vertical direction
HR horizontal direction

What is claimed is:

1. A modular processing system for biopharmaceutical processes, said modular processing system comprising:
at least one first processing unit and at least one second processing unit, configured to fluidically connect to each other;
at least one adapter plate configured to control at least one fluid flow from the first processing unit to the second processing unit;
such that the fluid flow between the first processing unit and the second processing unit is deflected at least partially by the adapter plate, and/or the fluid flow is controlled with the adapter plate in an open loop flow or in a closed loop flow,
wherein the adapter plate has an adapter channel configured to direct the fluid flow into the adapter channel through at least two inlet openings and out of the adapter channel through at least two outlet openings,
wherein at least a first of the inlet openings is arranged such that the fluid flow flows out of an outflow channel of the first processing unit into the adapter channel,
wherein at least a second of the inlet openings is arranged such that the fluid flow flows out of an inflow channel of the first processing unit into the adapter channel,
wherein at least a first of the outlet openings is arranged such that the fluid flow flows out of the first outlet opening into an outflow channel of the second processing unit, and
wherein at least a second of the outlet openings is arranged such that the fluid flow flows out of the second outlet opening into an inflow channel of the second processing unit.

2. The modular processing system as claimed in claim 1, wherein the adapter plate controls a pressure of the fluid flow.

3. The modular processing system as claimed in claim 1, wherein the at least one first processing unit comprises a plurality of first processing units connected in parallel, and/or wherein the at least one second processing unit comprises a plurality of second processing units connected in parallel, and wherein the first processing units form a first processing unit group and the second processing units form a second processing unit group.

4. The modular processing system as claimed in claim 1, wherein the at least one inlet opening is configured to be connected to an outflow channel of the first processing unit and/or
wherein the at least one outlet opening is configured to be connected to an inflow channel of the second processing unit.

5. The modular processing system as claimed in claim 1, wherein the adapter channel comprises:
a first channel region, which is arranged between the first inlet opening and the first outlet opening;
a second channel region, which is arranged between the second inlet opening and the second outlet opening; and
a connecting channel region, which fluidically connects the first and the second channel regions.

6. The modular processing system as claimed in claim 1, further comprising at least one deflection element arranged displaceably in the adapter channel such that the fluid flow is deflected by the adapter plate such that either:
a first fluid flow flows into the adapter channel through the first inlet opening and flows out through the first outlet opening; and a second fluid flow flows into the adapter channel through the second inlet opening and flows out of the adapter channel through the second outlet opening; or
the fluid flow flows into the adapter channel through the first inlet opening and flows out of the adapter channel through the second outlet opening.

7. The modular processing system as claimed in claim 5, further comprising two deflection elements configured as a multiway valve, wherein a first valve is arranged in the first channel region; and a second valve is arranged in the second channel region, wherein the valves are configured such that either:
a first fluid flow flows into the adapter channel through the first inlet opening and flows out through the first outlet opening; and a second fluid flow flows into the adapter channel through the second inlet opening and flows out of the adapter channel through the second outlet opening; or
the fluid flow flows into the adapter channel through the first inlet opening and flows out of the adapter channel through the second outlet opening.

8. The modular processing system as claimed in claim 7, wherein the multiway valve comprises a valve tube, which is arranged respectively displaceably in the first and the second channel region and is configured to be traversed in a corresponding manner by the first and the second fluid flow, wherein at least two valve openings are arranged in a lateral surface of the valve tube, said valve openings being arranged offset from one another in a direction of the displacement so that a fluid flow through the adapter channel is deflected as a function of a position of the displacement of the valve tube in the respective channel region.

9. The modular processing system as claimed in claim 1, further comprising at least one sensor arranged in or on the adapter channel.

10. The modular processing system as claimed in claim 1, wherein the adapter channel comprises at least one auxiliary input and/or at least one auxiliary output.

11. The modular processing system as claimed in claim 1, further comprising at least one pump arranged in or on the adapter channel.

12. The modular processing system as claimed in claim 11, wherein the pump is a peristaltic pump or piston pump.

13. The modular processing system as claimed in claim 1, further comprising at least one flow limiter arranged in the adapter channel.

\* \* \* \* \*